United States Patent
Aubert et al.

(10) Patent No.: US 7,626,054 B2
(45) Date of Patent: *Dec. 1, 2009

(54) BIAROMATIC COMPOUNDS WHICH ACTIVATE PPARγ-TYPE RECEPTORS AND COSMETIC/PHARMACEUTICAL COMPOSITIONS COMPRISED THEREOF

(75) Inventors: Jerome Aubert, Grasse (FR); Laurence Clary, La Colle sur Loop (FR); Pascale Mauvais, Antibes (FR); Michel Rivier, Nice (FR); Etienne Thoreau, Saint Vallier de Thiey (FR); Jean-Guy Boiteau, Saint Aunes (FR)

(73) Assignee: Galderma Research & Development, Biot (FR)

( * ) Notice: Subject to any disclaimer, the term of this patent is extended or adjusted under 35 U.S.C. 154(b) by 0 days.

This patent is subject to a terminal disclaimer.

(21) Appl. No.: 11/592,276

(22) Filed: Nov. 3, 2006

(65) Prior Publication Data

US 2007/0112070 A1 May 17, 2007

Related U.S. Application Data

(63) Continuation of application No. PCT/EP2005/005797, filed on Apr. 29, 2005.

(60) Provisional application No. 60/574,217, filed on May 26, 2004.

(30) Foreign Application Priority Data

May 6, 2004 (FR) .................................. 04 04913

(51) Int. Cl.
*C07C 241/00* (2006.01)
(52) U.S. Cl. ...................... 562/439; 562/405; 562/433; 560/19; 560/34
(58) Field of Classification Search ............ 560/19, 560/34; 562/405, 433, 439; 424/401
See application file for complete search history.

(56) References Cited

U.S. PATENT DOCUMENTS

2003/0134885 A1* 7/2003 Bernardon et al. .......... 514/369
2004/0039038 A1 2/2004 Bernardon et al.

FOREIGN PATENT DOCUMENTS

WO  WO 02/12210 A1  2/2002
WO  WO 2004/048351 A1  6/2004

OTHER PUBLICATIONS

STN CAPLUS abstract, Accession No. 2004:432769, Document No. 140:429035.*

* cited by examiner

*Primary Examiner*—Shailendra Kumar
*Assistant Examiner*—Sudhakar Katakam
(74) *Attorney, Agent, or Firm*—Buchanan, Ingersoll & Rooney P.C.

(57) ABSTRACT

Novel biaromatic compounds having the following structural formula (I):

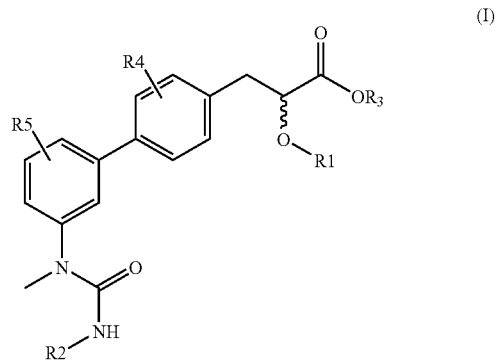

are formulated into pharmaceutical compositions suited for administration in human or veterinary medicine, in particular in dermatology as well as in the fields of cardiovascular diseases, immune diseases and/or diseases related to the metabolism of lipids, or, alternatively, into cosmetic compositions.

56 Claims, 2 Drawing Sheets

BIAROMATIC COMPOUNDS WHICH ACTIVATE PPARγ-TYPE RECEPTORS AND COSMETIC/PHARMACEUTICAL COMPOSITIONS COMPRISED THEREOF

CROSS-REFERENCE TO PRIORITY/PCT/PROVISIONAL APPLICATIONS

This application claims priority under 35 U.S.C. § 119 of FR 04/04913, filed May 6, 2004, and of U.S. Provisional Application No. 60/574,217, filed May 26, 2004, and is a continuation of PCT/EP 2005/005797 filed Apr. 29, 2005 and designating the United States, published in the English language as WO 2005/108352 A1 on Nov. 17, 2005, each hereby expressly incorporated by reference and each assigned to the assignee hereof.

BACKGROUND OF THE INVENTION

1. Technical Field of the Invention

The present invention relates to a novel class of biaromatic compounds which are activators of receptors of "Peroxisome Proliferator-Activated Receptor" type of subtype γ (PPARγ). This invention also relates to their process of preparation and to their formulation into pharmaceutical compositions suited for human or veterinary medicine, or alternatively for cosmetic compositions.

2. Description of Background and/or Related and/or Prior Art:

The activity of receptors of PPAR type has been the subject of many studies. Mention may be made, by way of indication, of the publication entitled "Differential Expression of Peroxisome Proliferator-Activated Receptor Subtypes During the Differentiation of Human Keratinocytes", Michel Rivier et al., J. Invest. Dermatol., 1998, 111, 1116-1121, in which a large number of bibliographic references relating to receptors of PPAR type are listed. Mention may also be made, by way of indication, of the report entitled "The PPARs: From Orphan Receptors to Drug Discovery", Timothy M. Willson et al., J. Med. Chem., 2000, 43, 527-550.

PPAR receptors activate transcription by binding to elements of DNA sequences, known as peroxisome proliferator response elements (PPRE), in the form of a heterodimer with retinoid X receptors (known as RXRs).

Three subtypes of human PPARs have been identified and described: PPARα, PPARγ and PPARδ (or NUC1).

PPARα is mainly expressed in the liver, while PPARδ is ubiquitous.

PPARγ is the most widely studied of the three subtypes. All prior art references suggest a critical role for PPARγ in the regulation of the differentiation of adipocytes, where it is greatly expressed. It also plays a key role in systemic lipid homeostasis.

Furthermore, the assignee hereof has already disclosed, in FR 98/02894, the use of PPARγ-activating compounds in the preparation of a pharmaceutical composition, the composition being intended for the treatment of skin disorders related to an anomaly in the differentiation of the epidermal cells.

The assignee hereof has also disclosed a class of biaromatic compounds which are activators of PPARγ receptors in FR-2,812,876.

SUMMARY OF THE INVENTION

A novel class of PPARγ-activating compounds has now been developed exhibiting biological activities which are significantly improved with respect to those of the compounds known to the prior art and in particular with respect to those described in FR-2,812,876.

According to the present invention, a restricted group of compounds has now been developed, corresponding to the formula (I) below, which exhibit a surprising biological activity, in particular a binding affinity for PPARγ receptors which is significantly increased with respect to that of the compounds of FR-2,812,876. This increased binding affinity emerges in particular from apparent dissociation constant (KdApp) values which are surprisingly lowered, as more fully explained below.

Thus, the present invention features novel compounds corresponding to the following general formula (I):

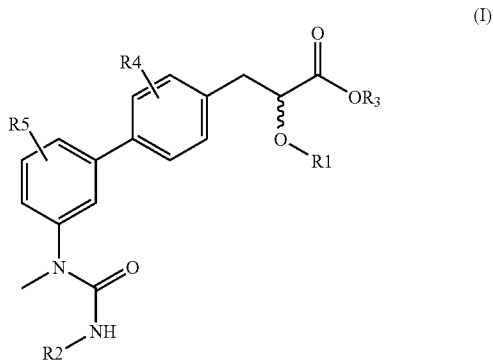

in which:

R1 is an alkyl radical having 1 to 6 carbon atoms, an acetyl group, a methylcyclopropane group, an aralkyl radical or an aryl radical;

R2 is an alkyl radical having 3 to 8 carbon atoms;

R3 is a hydrogen atom or an alkyl radical having 1 to 6 carbon atoms;

R4 and R5, which may be identical or different, are each a hydrogen atom, a halogen atom, a hydroxyl radical, an alkyl radical having from 1 to 6 carbon atoms, an alkoxy radical, a benzyloxy radical or a trifluoromethyl radical;

and the isomers, optical and/or geometrical, pure or as a mixture, in all proportions, of the said compounds of formula (I) and the tautomeric forms, and also the salts of the said compounds of formula (I).

Figure 1:
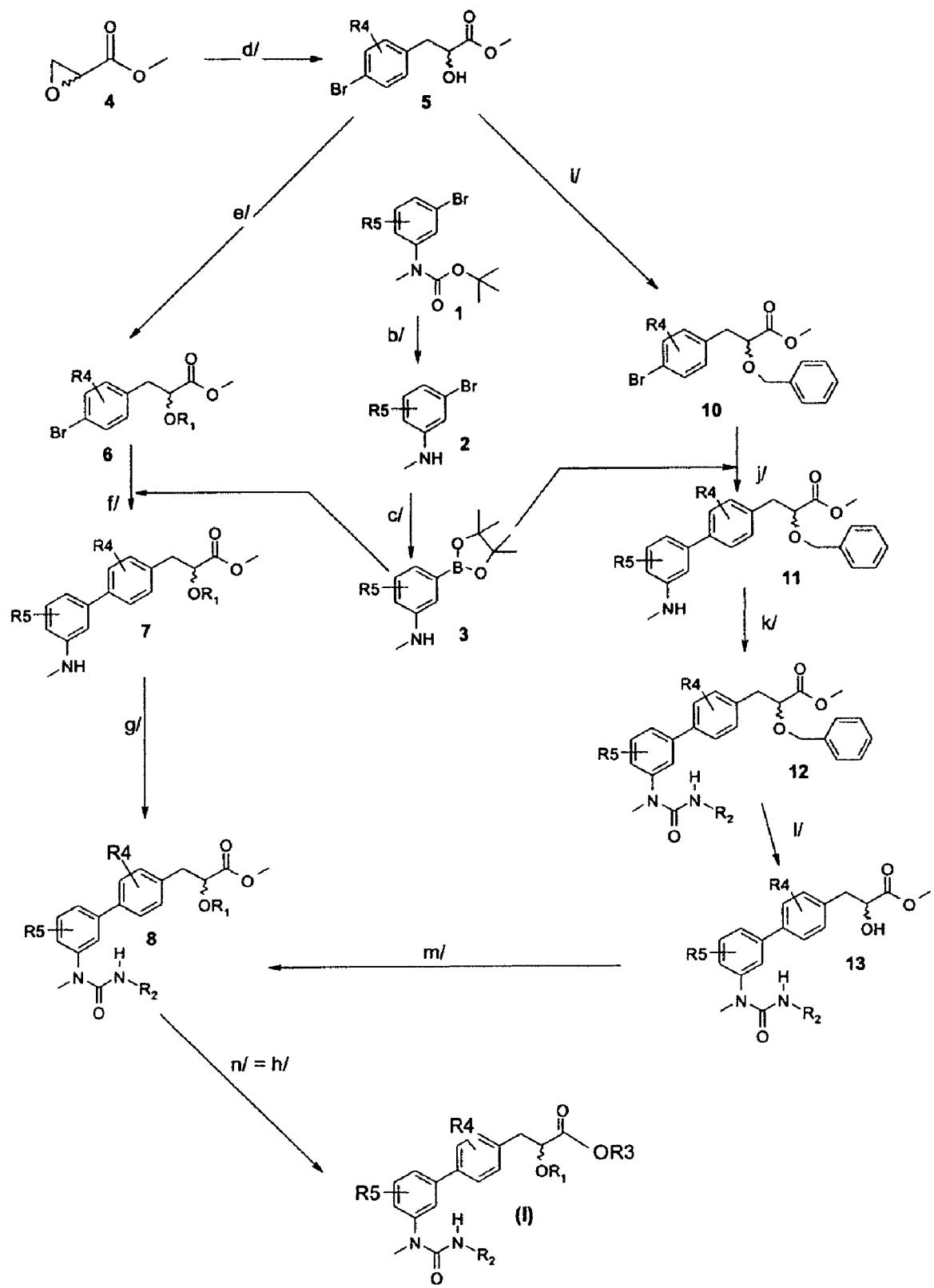
FIGS. 1 and 2 illustrate a variety of reaction schemes for the preparation of the compounds according to the present invention.

DETAILED DESCRIPTION OF BEST MODE AND SPECIFIC/PREFERRED EMBODIMENTS OF THE INVENTION

For the compounds of formula (I) which is presented above, the term "geometrical isomer" means cis/trans or E/Z isomerism. More particularly, the possible double bond or bonds present in the various substituents of the compounds of general formula (I) can be of E or Z configuration. These geometrical isomers, pure or impure, alone or as a mixture, are an integral part of the compounds of formula (I).

The term "optical isomer" embraces all the forms of isomers, alone or as a mixture, the presence of which results from one or more axes and/or centres of symmetry in the molecule which results in the rotation of a beam of polarized light. The term "optical isomer" comprises more particularly the enantiomers and the diastereoisomers, in the pure form or as a mixture.

When the compounds according to the invention are provided in the form of a salt, they are preferably an alkali metal salt, in particular the sodium salt, or an alkaline earth metal salt or an organic amine salt, more particularly of amino acids, such as arginine or lysine.

According to the present invention, the term "alkyl radical having from 1 to 6 carbon atoms" means, preferably, an optionally branched, saturated or unsaturated, linear or cyclic alkyl radical selected from the methyl, ethyl, n-propyl, isopropyl, cyclopropyl, n-butyl, isobutyl, tert-butyl, n-pentyl, isopentyl, n-hexyl, isohexyl, cyclohexyl, ethylenyl, allyl, propenyl, butenyl, pentenyl or hexenyl radicals.

According to the present invention, the term "alkyl radical having from 3 to 8 carbon atoms" means, preferably, an optionally branched, saturated or unsaturated, linear or cyclic alkyl radical comprising 3 to 8 carbon atoms and preferably the n-propyl, isopropyl, cyclopropyl, n-butyl, isobutyl, tert-butyl, n-pentyl, isopentyl, cyclopentyl, n-hexyl, isohexyl, cyclohexyl, n-heptyl, isoheptyl, n-octyl, isooctyl, allyl, propenyl, butenyl, pentenyl, hexenyl, heptenyl or octenyl radicals.

The term "halogen atom" means, preferably, a fluorine, chlorine or bromine atom.

The term "aralkyl radical" means, preferably, a benzyl, phenethyl or naphth-2-ylmethyl radical which is unsubstituted or substituted by one or more radicals selected from among a halogen atom, a $CF_3$ radical, an alkyl radical having from 1 to 6 carbon atoms, an alkoxy radical having from 1 to 6 carbon atoms, a hydroxyl radical or an amino functional group which is unprotected or unsubstituted or optionally substituted by at least one alkyl radical having from 1 to 6 carbon atoms, or a carboxyl functional group.

The term "aryl radical" means, preferably, a phenyl, biphenyl, cinnamyl or naphthyl radical which can be mono-or disubstituted by a halogen atom, a $CF_3$ radical, an alkyl radical having from 1 to 6 carbon atoms, an alkoxy radical having from 1 to 6 carbon atoms, a nitro functional group, a polyether radical, an aryl radical, a benzoyl radical, an alkyl ester group, a carboxylic acid, a hydroxyl radical optionally protected by an acetyl or benzoyl group, or an amino functional group optionally protected by an acetyl or benzoyl group or optionally substituted by at least one alkyl having from 1 to 6 carbon atoms.

The term "alkoxy radical" means, preferably, a methoxy, ethoxy, isopropyloxy, tert-butoxy, hexyloxy, benzyloxy or phenoxy radical which can optionally be substituted by an alkyl radical having from 1 to 6 carbon atoms.

The term "polyether radical" means, preferably, a radical having from 1 to 6 carbon atoms which is interrupted by at least one oxygen atom, such as the methoxymethoxy, methoxymethylene, ethoxymethoxy, ethoxymethylene or methoxyethoxymethoxy radicals.

The term "alkyl ester radical" means a carboxylate functional group substituted by an alkyl radical having from 1 to 6 carbon atoms.

Among the compounds of formula (I) above within the scope of the present invention, the following compounds (alone or as a mixture) are particularly exemplary:

1. 2(S)-Ethoxy-3-[3'-(3-heptyl-1-methylureido)biphenyl-4-yl]propanoic acid,
2. 2(S)-Ethoxy-3-[3'-(1-methyl-3-pentylureido)biphenyl-4-yl]propanoic acid,
3. 2(S)-Cyclopropylmethoxy-3-[3'-(3-heptyl-1-methylureido)biphenyl-4-yl]propanoic acid,
4. 2(S)-Propyloxy-3-[3'-(3-heptyl-1-methylureido)biphenyl-4-yl]propanoic acid,
5. 2(S)-Benzyloxy-3-[3'-(3-heptyl-1-methylureido)biphenyl-4-yl]propanoic acid,
6. 2(S)-Allyloxy-3-[3'-(3-heptyl-1-methylureido)biphenyl-4-yl]propanoic acid,
7. 2(S)-Cyclopropylmethoxy-3-[3'-(1-methyl-3-pentylureido)biphenyl-4-yl]propanoic acid,
8. 3-[3'-(1-Methyl-3-pentylureido)biphenyl-4-yl]-2(S)-propoxypropanoic acid,
9. 2(S)-Allyloxy-3-[3'-(1-methyl-3-pentylureido)biphenyl-4-yl]propanoic acid,
10. 2(S)-Benzyloxy-3-[3'-(1-methyl-3-pentylureido)biphenyl-4-yl]propanoic acid,
11. 2(S)-Methoxy-3-[3'-(1-methyl-3-pentylureido)biphenyl-4-yl]propanoic acid,
12. 3-[3'-(3-Heptyl-1-methylureido)biphenyl-4-yl]-2(S)-methoxypropanoic acid,
13. 2(S)-Ethoxy-3-[3'-(1-methyl-3-propylureido)biphenyl-4-yl]propanoic acid,
14. 3-[3'-(3-Cyclopropylmethyl-1-methylureido)biphenyl-4-yl]-2(S)-ethoxypropanoic acid,
15. 3-[3'-(3-Cyclopentylmethyl-1-methylureido)biphenyl-4-yl]-2(S)-ethoxypropanoic acid,
16. 2(S)-Ethoxy-3-[3-fluoro-3'-(1-methyl-3-pentylureido)biphenyl-4-yl]propanoic acid,
17. 2(S)-Ethoxy-3-[4'-fluoro-3'-(1-methyl-3-pentylureido)biphenyl-4-yl]propanoic acid,
18. 3-[3,4'-Difluoro-3'-(1-methyl-3-pentylureido)biphenyl-4-yl]-2(S)-ethoxypropanoic acid,
19. Methyl 2(S)-ethoxy-3-[3'-(3-heptyl-1-methylureido)biphenyl-4-yl]propanoate,
20. Methyl 2(S)-cyclopropylmethoxy-3-[3'-(1-methyl-3-pentylureido)biphenyl-4-yl]propanoate,
21. 2(S)-Cyclopropylmethoxy-3-[3'-(3-cyclopropylmethyl-1-methylureido)biphenyl-4-yl]propanoic acid,
22. 3-{3'-[3-(2-Cyclohexylethyl)-1-methylureido]biphenyl-4-yl}-2(S)-ethoxypropanoic acid,
23. 2(R)-Ethoxy-3-[3'-(1-methyl-3-pentylureido)biphenyl-4-yl]propanoic acid,
24. 2(R)-Ethoxy-3-[3'-(3-heptyl-1-methylureido)biphenyl-4-yl]propanoic acid,
25. 2-Ethoxy-3-[3'-(3-heptyl-1-methylureido)biphenyl-4-yl]propanoic acid,
26. 2(R)-Allyloxy-3[3'-(3-heptyl-1-methylureido)biphenyl-4-yl]propanoic acid,
27. 3-[3'-(3-Allyl-1-methylureido)biphenyl-4-yl]-2(S)-ethoxypropanoic acid,
28. Allyl 3-[3'-(3-allyl-1-methylureido)biphenyl-4-yl]-2(S)-ethoxypropanoate.

According to the present invention, the compounds of formula (I) which are more particularly preferred are those which exhibit at least one of the following characteristics:

R1 is an alkyl radical selected from among the methyl, ethyl, n-propyl, isopropyl, cyclopropyl, n-butyl, isobutyl or tert-butyl radicals, a methylcyclopropane group or a benzyl radical, R2 is an alkyl radical selected from among the n-pentyl, isopentyl, cyclopentyl, n-hexyl, isohexyl, cyclohexyl, n-heptyl or isoheptyl radicals, R3 is a hydrogen atom, R4 and/or R5 are a hydrogen atom or a fluorine atom.

In particular, according to the present invention, preferred are the compounds of formula (I) exhibiting all of the following characteristics:

R1 is an alkyl radical selected from among the methyl, ethyl, n-propyl, isopropyl, cyclopropyl, n-butyl, isobutyl or tert-butyl radicals, a methylcyclopropane group or a benzyl radical, R2 is an alkyl radical selected from among the n-pentyl, isopentyl, cyclopentyl, n-hexyl, isohexyl, cyclohexyl, n-heptyl or isoheptyl radicals, R3 is a hydrogen atom, R4 and/or R5 are a hydrogen atom or a fluorine atom.

More particularly, the present invention features a process for the synthesis of the compounds corresponding to the general formula (I) or of the possible isomers, optical and/or geometrical, pure or as a mixture, in all proportions, of the said compounds of formula (I), of the possible tautomeric forms, or of the salts of the said compounds of formula (I), comprising the following stages:

in the stages described below, which relate to FIG. 1, unless otherwise indicated, the R1, R2, R3, R4 and R5 radicals of the compounds 1 to 20 are the same as those defined for the compounds of general formula (I).

a) Preparation of the compound of formula 1:

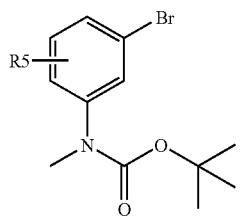

1 from commercial 3-bromoaniline optionally substituted by an R5 group, by protecting the amine with di(tert-butyl) dicarbonate and by then carrying out a methylation, for example with methyl iodide, in the presence of sodium hydride;

b) Preparation of compound 2:

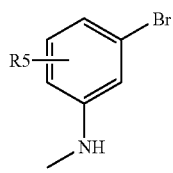

2 by treating compound 1 with an acid, such as, for example, trifluoroacetic acid;

c) Preparation of compound 3:

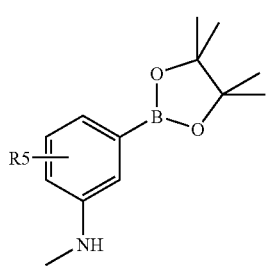

3 by the reaction of compound 2 with pinacolborane in the presence of a catalyst, such as palladium dichloride diphenylphosphinopropane ferrocene;

d) Preparation of compound 5:

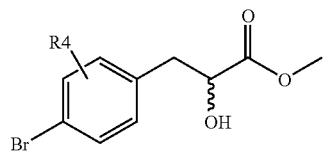

5 by treating the commercial epoxide 4:

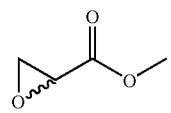

4 with an aryl cuprate obtained by reaction of an aryl halide, such as, for example, 1,4-dibromobenzene, in the presence of tert-butyllithium and of copper cyanide;

e) Preparation of compound 6:

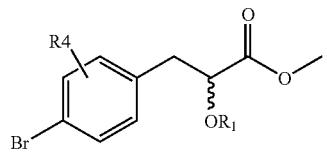

6 by reacting compound 5 with an alkyl halide, such as ethyl iodide, for example, in the presence of silver oxide, to prevent any problem of racemization;

f) Preparation of compound 7:

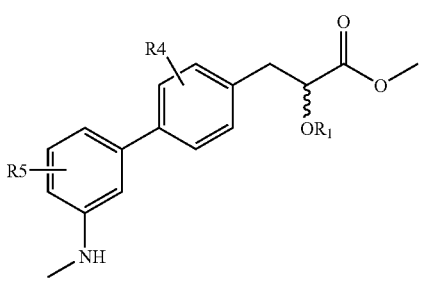

7 by the coupling of compound 6 and compound 3 according to a reaction of Suzuki type in the presence of tetrakis(triphenylphosphine)palladium;

g) Preparation of compound 8:

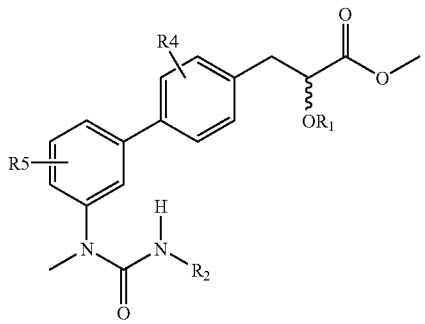

by the reaction from compound 7 and an alkyl isocyanate, such as, for example, heptyl isocyanate;

h) Preparation of compound (I):

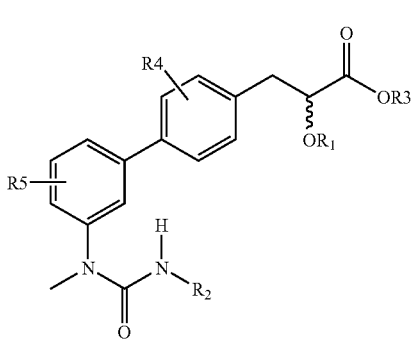

h1) when R3 is an alkyl radical: by transesterification of compound 8 with an alcohol in the presence of an acid, such as sulfuric acid, or h2) when R3 is a hydrogen atom: by saponification of compound 8 in the presence of a base, such as, for example, sodium hydroxide.

According to another advantageous process for the synthesis of the compounds of formula (I), the stages for preparing compound 3 are repeated as defined in parts a) to c) and the stages for preparing compound 5 are repeated as defined in part d) and are followed by the stages set out below:

i) Preparation of compound 10:

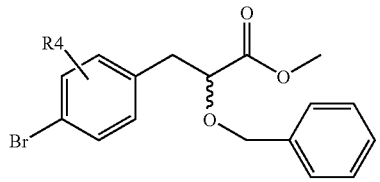

by treating compound 5 with a benzyl halide, such as, for example, benzyl bromide, in the presence of silver oxide;

j) Preparation of compound 11:

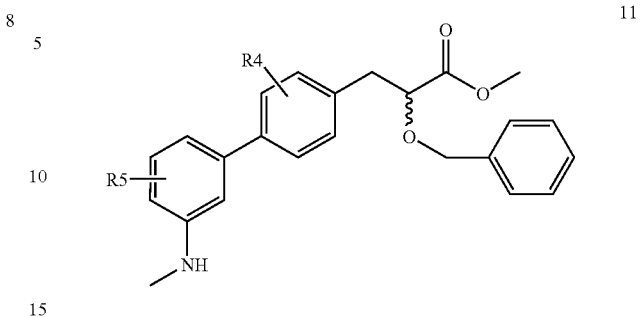

by coupling compound 10 with compound 3 by a reaction of Suzuki type using a palladium catalyst, such as, for example, tetrakis(triphenylphosphine)palladium;

k) Preparation of compound 12:

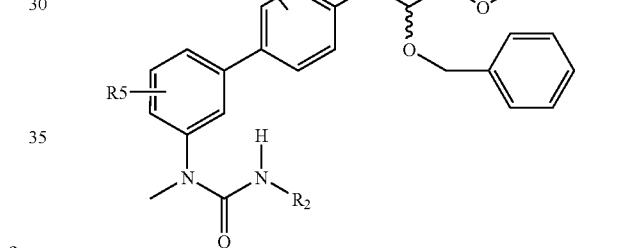

by the reaction from compound 11 and an alkyl isocyanate, such as, for example, heptyl isocyanate;

l) Preparation of the alcohol 13:

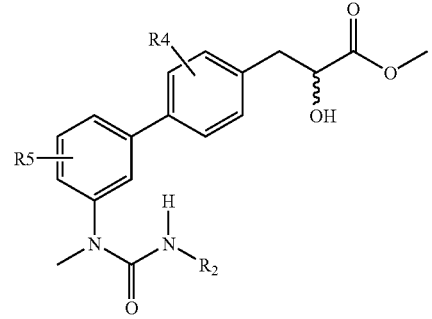

by hydrogenolysis of compound 12 with hydrogen in the presence of palladium-on-charcoal;

m) Preparation of compound 8:

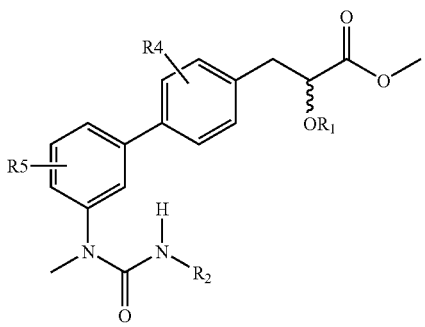

by reacting compound 13 with an alkyl halide, such as allyl bromide, for example, in the presence of silver oxide;

n) Preparation of compound (I) from compound 8 as defined in stage h), the alternatives n1) and n2) being identical to the alternatives h1) and h2).

Figure 2:
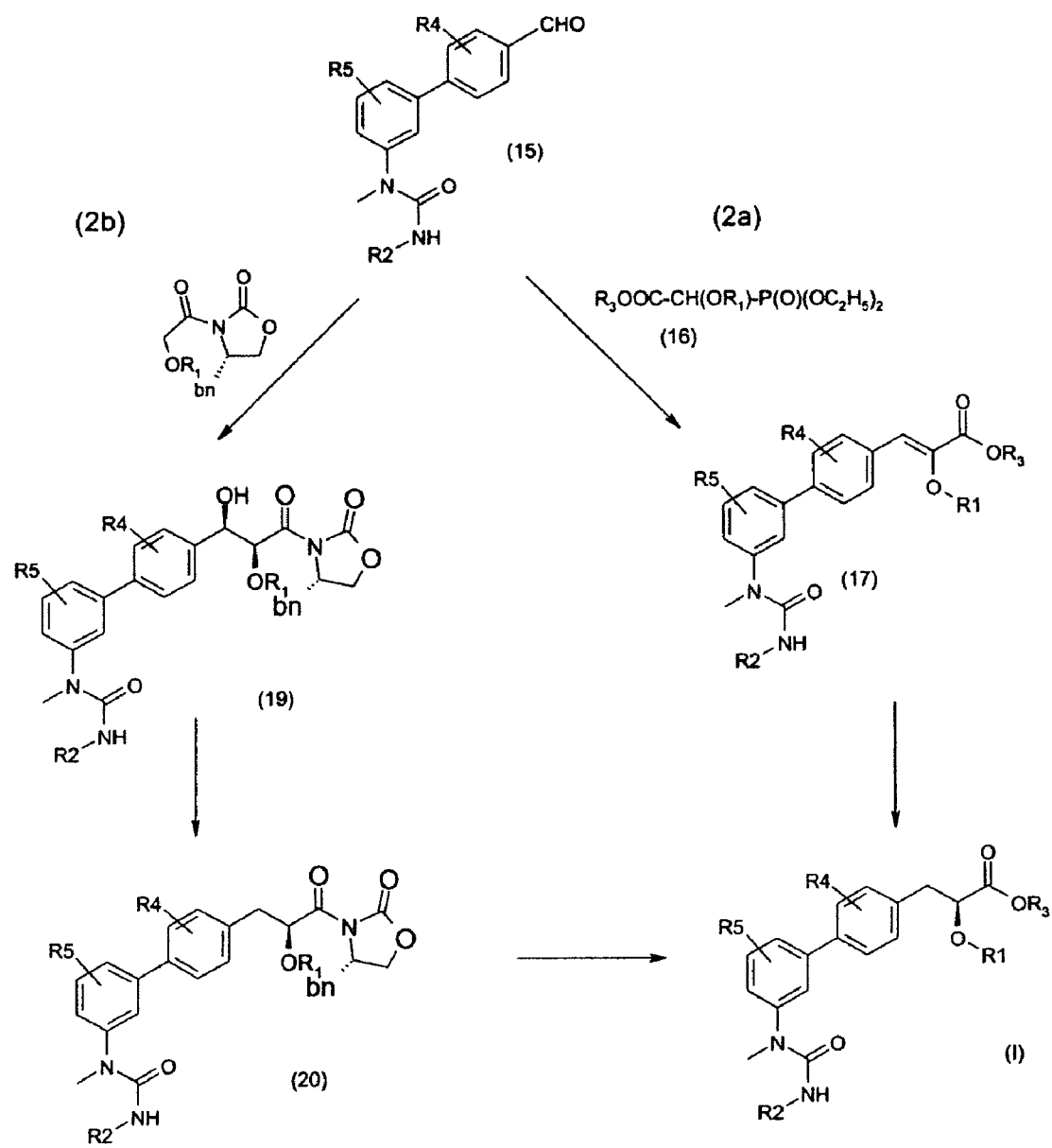

The compounds of formula (I) can also be obtained according to the reaction scheme presented by the synthetic route 2a of FIG. 2 from aldehyde derivatives 15 according to a reaction of Horner type with a phosphonate 16 in the presence of a base, such as sodium hydride, butyllithium or potassium tert-butoxide, then hydrogenation in the presence of palladium-on-charcoal and optionally enzymatic resolution, for example in the presence of the enzyme proteinase 2A, to obtain the (S) enantiomer. According to this method of synthesis, R1, R2, R3, R4 and R5 are as defined above.

The compounds of formula (I) can also be obtained according to the reaction scheme presented by the synthetic route 2b of FIG. 2 by the reaction of 4(S)-benzyloxazolidin-2-one and of a 2-alkoxyacetic acid chloride for the preparation of an Evans derivative, followed by the condensation of such an Evans derivative, of well-defined chirality, with the aldehyde derivative 15 in the presence of dibutylboron triflate, for example, which results in the derivative 19. The deoxygenation of compound 19 by the Barton reaction results in compound 20. Compound (I) is obtained from compound 20 by saponification, for example in the presence of lithium hydroxide, or by transesterification, for example with sodium methoxide in methanol. According to this method of synthesis, R1, R2, R3, R4 and R5 are as defined above.

According to the present invention, the term "Evans derivative" means, preferably, an oxazolidin-2-one derivative of well-defined chirality, such as a 4(S)-benzyloxazolidin-2-one derivative.

According to the present invention, the term "Barton reaction" means the reaction of phenyl chlorothionoformate with the hydroxyl group of compound 19, in the case of the synthetic route 2b considered in FIG. 2, followed by a radical reaction in the presence of tributyltin hydride.

The compounds according to the invention exhibit modulatory properties with regard to receptors of PPAR type. This activity on PPARα, δ and γ receptors is measured in a transactivation test and quantified by the apparent dissociation constant (KdApp), as described in Example 7 below.

In a manner not obvious to one skilled in the art in the light of the prior art, the preferred compounds according to the invention exhibit a surprising biological activity, in particular a binding affinity for PPARδ receptors which is significantly increased with respect to that of the compounds according to FR-2,812,876. The KdApp values of the compounds according to the present invention for PPARγ receptors are listed in Example 7 and are illustrated in Table 1, where they are compared with those of the compounds of FR-2,812,876: it is apparent that they are less than 1 nM and advantageously less than 0.1 nM, i.e., at least 120 times lower and up to several thousand times lower than the KdApp values described for the compounds of FR-2,812,876 (Table 1), reflecting a considerably increased affinity of the compounds according to the present invention for PPARγ receptors. In Table 1, the KdApp values, with PPARγ receptors, of certain compounds according to the invention are compared with certain compounds according to the prior art, the compounds exhibiting similar substituents being considered. In particular, the R1 radical according to the invention is equivalent to the R10 radical of the compounds according to FR-2,812,876 and the R2 radical according to the invention is equivalent to the R4 radical of the compounds according to FR-2,812,876.

In particular, the compounds according to the invention are modulators of specific receptors of PPARγ type, that is to say that they exhibit a ratio of the KdApp for the PPARα or PPARδ receptors to the KdApp for the PPARγ receptors of greater than or equal to 10. Preferably, this PPARα/PPARγ or PPARδ/PPARγ ratio is greater than or equal to 50 and more advantageously greater than or equal to 100.

The present invention also features the compounds of formula (I) as described above as medicaments.

The compounds according to the invention are particularly well suited for the following treatments:

1) of dermatological conditions linked to a disorder of keratinization involving differentiation and proliferation, in particular for treating acne vulgaris, comedonic or polymorphic acne, acne rosacea, nodulocystic acne, acne conglobata, senile acne and secondary acnes, such as solar, drug or occupational acne, 2) of other types of disorders of keratinization, in particular ichthyoses, ichthyosiform conditions, Darrier's disease, palmoplantar keratoderma, leucoplakia and leucoplakiform conditions or cutaneous or mucosal (oral) lichen, 3) of other dermatological conditions or afflictions having an inflammatory immunoallergic component, with or without cell proliferation disorder, and, in particular, all forms of psoriasis, whether cutaneous, mucosal or ungual, and even psoriatic rheumatism, or alternatively cutaneous atopy, such as eczema, or respiratory atopy or alternatively gingival hypertrophy, 4) of all dermal or epidermal proliferations, whether they are benign or malignant and whether they are or are not of viral origin, such as common warts, flat warts and epidermodysplasia verruciformis, florid or oral papillomatoses, T lymphoma, and the proliferations which can be induced by ultraviolet radiation, in particular in the case of basal cell and prickle cell epithelioma, and also all precancerous skin lesions, such as keratoacanthomas, 5) of other dermatological disorders, such as immune dermatoses, such as lupus erythematosus, immune bullous diseases and collagen diseases, such as scleroderma, 6) of dermatological or general conditions or afflictions having an immunological component, 7) of skin disorders due to exposure to UV radiation, and also for repairing or combating skin aging, whether photoinduced or chronologic or for reducing actinic keratoses and pigmentations or any pathology associated with chronologic or actinic aging, such as xerosis, 8) of disorders of the sebaceous function, such as hyperseborrhoea of acne or simple seborrhoea, 9) or the prevention of disorders of cicatrization or the prevention or the repair of stretch marks, 10) of disorders of pigmentation, such as hyperpigmentation, melasma, hypopigmentation or vitiligo, 11) of conditions of the metabolism of lipids, such as obesity, hyperlipidaemia or non-insulin-dependent diabetes, 12) of inflammatory conditions, such as arthritis, 13) or the prevention of cancerous or precancerous conditions, 14) or the prevention of alopecia of various origins, in particular alopecia due to chemotherapy or to radiation, 15) of disorders of the immune system, such as asthma, type I diabetes mellitus, multiple sclerosis or other selective dysfunctions of the immune system, 16) of conditions of the cardiovascular system, such as arteriosclerosis or hypertension.

The present invention also features pharmaceutical or cosmetic compositions comprising, formulated into a physiologically acceptable medium, at least one compound of formula (I) as defined above.

This invention also features the use of the compounds of formula (I) in the manufacture of compositions suited for the treatment of the abovementioned conditions, in particular for regulating and/or restoring the metabolism of skin lipids.

The compositions according to the invention can be administered orally, parenterally, topically or ocularly. Preferably, the pharmaceutical composition is packaged in a form suitable for topical application.

Orally, the composition, more particularly the pharmaceutical composition, can be provided in the form of tablets, including sugar-coated tablets, hard gelatin capsules, syrups, suspensions, solutions, powders, granules, emulsions or lipid or polymeric microspheres or nanospheres or vesicles which make possible controlled release. Parenterally, the composition can be provided in the form of solutions or suspensions for infusion or for injection.

The compounds according to the invention are generally administered at a daily dose of approximately 0.001 mg/kg to 100 mg/kg of body weight, taken 1 to 3 times.

The compounds are administered systemically at a concentration generally of from 0.001% to 10% by weight, preferably from 0.01% to 1% by weight, with respect to the weight of the composition.

Topically, the pharmaceutical composition according to the invention is more particularly suited for the treatment of the skin and mucous membranes and can be provided in the form of salves, creams, milks, ointments, powders, impregnated pads, solutions, gels, sprays, lotions or suspensions. It can also be provided in the form of lipid or polymeric microspheres or nanospheres or vesicles or of polymeric patches and of hydrogels which make possible controlled release. This topical composition can be provided in the anhydrous form, in the aqueous form or in the form of an emulsion.

The compounds are administered topically at a concentration generally of from 0.001% to 10% by weight, preferably from 0.01% to 1% by weight, with respect to the total weight of the composition.

The compounds of formula (I) according to the invention also have an application in the cosmetics field, in particular in body and hair hygiene and more particularly for regulating and/or restoring the metabolism of skin lipids. In comparison with the products known previously, these compounds of formula (I) have the advantage of additionally exhibiting other advantageous properties, in particular anti-inflammatory or soothing properties, which makes them less irritating and therefore better tolerated compounds.

The present invention also features the cosmetic use of a composition comprising, formulated into a physiologically acceptable vehicle, at least one of the compounds of formula (I) for body or hair hygiene.

The cosmetic compositions according to the invention, comprising, in a cosmetically acceptable vehicle, at least one compound of formula (I) or one of its optical or geometrical isomers or one of its salts, can be provided in particular in the form of a cream, a milk, a lotion, a gel, lipid or polymeric microspheres or nanospheres or vesicles, a soap or a shampoo.

The concentration of compound of formula (I) in the subject cosmetic compositions ranges from 0.001% to 3% by weight, with respect to the total weight of the composition.

The compositions as described above can, of course, additionally comprise inert or even pharmacodynamically active additives or combinations of these additives and in particular: wetting agents; depigmenting agents, such as hydroquinone, azelaic acid, caffeic acid or kojic acid; emollients; moisturizing agents, such as glycerol, polyethylene glycol (PEG) 400, thiamorpholinone and its derivatives, or urea; anti-seborrhoeic or anti-acne agents, such as S-carboxymethylcysteine, S-benzylcysteamine, their salts or their derivatives, or benzoyl peroxide; anti-fungal agents, such as ketoconazole or 4,5-polymethylene-3-isothiazolidones; anti-bacterials; carotenoids and in particular β-carotene; anti-psoriatic agents, such as anthralin and its derivatives; eicosa-5,8,11,14-tetraynoic and eicosa-5,8,11-triynoic acids, their esters and amides; and, finally, retinoids. The compounds of formula (I) can also be combined with vitamins D or their derivatives, with corticosteroids, with agents for combating free radicals, with α-hydroxy or α-keto acids or their derivatives, or with ion-channel blockers.

These compositions can also comprise flavor enhancers, preservatives, such as esters of para-hydroxybenzoic acid, stabilizing agents, moisture-regulating agents, pH-regulating agents, agents for modifying osmotic pressure, emulsifying agents, UV-A and UV-B screening agents, or antioxidants, such as α-tocopherol, butylated hydroxyanisole or butylated hydroxytoluene.

Of course, one skilled in this art will take care to select the optional compound or compounds to be added to these compositions so that the advantageous properties intrinsically associated with the present invention are not, or not substantially, detrimentally affected by the envisaged addition.

The present invention also features a cosmetic regime or regimen for rendering the skin more attractive, wherein a composition comprising at least one compound of formula (I) as defined above is topically applied onto the skin. The regulation and/or the restoration of the metabolism of skin lipids makes it possible to obtain skin with a surface appearance which has been rendered more attractive.

In order to further illustrate the present invention and the advantages thereof, the following specific examples of active compounds are given, as are the results of the biological activities thereof, it being understood that same are intended only as illustrative and in nowise limitative. In said examples to follow, all parts and percentages are given by weight, unless otherwise indicated.

EXAMPLE 1

Synthesis of 2(S)-Ethoxy-3-[3'-(3-heptyl-1-methylureido)biphenyl-4-yl]propanoic acid a) Preparation of tert-Butyl (3-bromophenyl)carbamate:

120 g (549 mmol) of di(tert-butyl) dicarbonate are added in small amounts at ambient temperature to a mixture of 94 g (549 mmol) of 3-bromoaniline and 1 l of dichloromethane. After stirring for 18 hours, the reaction mixture is poured into ice-cold water and extracted with dichloromethane. The organic phase is separated by settling, dried over magnesium sulfate and evaporated. 138 g of tert-butyl (3-bromobenzyl) carbamate are obtained. Yield=98%.

b) Preparation of tert-Butyl (3-bromophenyl)-N-methylcarbamate:

19 g (475 mmol) of sodium hydride (60% in oil) are added in small amounts to a solution of 114 g (447 mmol) of tert-butyl (3-bromobenzyl)carbamate in 800 ml of dimethylformamide and the reaction medium is stirred until evolution of gas has ceased. 29.3 ml (470 mmol) of methyl iodide are added dropwise and stirring is maintained for 18 hours. The reaction medium is poured into ice-cold water and extracted with ethyl acetate. The organic phase is separated by settling, dried over magnesium sulfate and evaporated. 115 g of tert-butyl (3-bromobenzyl)-N-methylcarbamate are obtained. Yield=95%.

c) Preparation of tert-Butyl (4'-formylbiphenyl-3-yl)methylcarbamate:

307 ml (615 mmol) of an aqueous potassium carbonate solution (2M) are added dropwise to a mixture of 61.5 g (205 mmol) of tert-butyl (3-bromobenzyl)-N-methylcarbamate, 46 g (307 mmol) of 4-formylbenzeneboronic acid and 500 ml of toluene. The reaction medium is subsequently degassed with argon and 7 g (6.2 mmol) of tetrakis(triphenylphosphine)palladium(0) are added. After heating at 90° C. for 24 hours, the reaction medium is poured into water and extracted with ethyl acetate. The organic phase is separated by settling, dried over magnesium sulfate and evaporated. The residue obtained is purified by chromatography on a silica column eluted with a mixture of heptane and ethyl acetate (70/30). After evaporating the solvents, 67 g of tert-butyl (4'-formyl-biphenyl-3-yl)methylcarbamate are collected. Yield=60%.

d) Preparation of tert-Butyl {4'-[3-(4(S)-benzyl-2-oxooxazolidin-3-yl)-2(S)-ethoxy-1(R)-hydroxy-3-oxopropyl]biphenyl-3-yl}methylcarbamate:

72.3 ml (72.3 mmol) of dibutylboron triflate and then 12.6 ml (72.3 mmol) of diisopropylethylamine are added dropwise to a solution, cooled to 0° C., of 15.2 g (57.8 mmol) of (S)-4-benzyl-3-(2-ethoxyacetyl)oxazolidin-2-one, prepared as described in the publication by Bernard Hulin et al., *J. Med. Chem.*, 1996, 39, 3897-3907, from commercial (S)-4-benzyloxazolidin-2-one, in 150 ml of dichloromethane. The reaction medium is stirred at 0° C. for 30 min and then cooled to −78° C. A solution of 15 g (48.2 mmol) of tert-butyl (4'-formylbiphenyl-3-yl)methylcarbamate in 70 ml of dichloromethane is then added dropwise. After stirring from −78° C. to ambient temperature over 4 hours, the reaction medium is cooled to 0° C. and a mixture of 130 ml of a buffer solution, pH=7, and of 100 ml of methanol is added dropwise, followed by the dropwise addition of a mixture of 130 ml of aqueous hydrogen peroxide solution and of 100 ml of methanol. The reaction medium is stirred at 0° C. for 1 hour and then at ambient temperature for 3 hours. After addition of water, the reaction medium is extracted with dichloromethane. The organic phase is dried over magnesium sulfate, filtered and evaporated under vacuum. The residue obtained is purified by chromatography on a silica column eluted with a mixture of heptane and ethyl acetate (70/30) and then increase in the polarity up to a 50/50 heptane/ethyl acetate mixture. After evaporation of the solvents, 28 g of tert-butyl {4'-[3-(4(S)-benzyl-2-oxooxazolidin-3-yl)-2(S)-ethoxy-1 (R)-hydroxy-3-oxopropyl]biphenyl-3-yl}methylcarbamate are collected. Yield=81%.

e) Preparation of tert-Butyl (S)-{4'-[3-(4-benzyl-2-oxooxazolidin-3-yl)-2-ethoxy-3-oxopropyl]biphenyl-3-yl}methylcarbamate:

4.8 ml (9.6 mmol) of sodium bis(trimethylsilylamide) are added dropwise to a solution, cooled beforehand to 0° C., of 5 g (8.7 mmol) of tert-butyl {4'-[3-(4(S)-benzyl-2-oxooxazolidin-3-yl)-2(S)-ethoxy-1(R)-hydroxy-3-oxopropyl]biphenyl-3-yl}methylcarbamate in 70 ml of tetrahydrofuran. The reaction medium is stirred at −78° C. for 1 hour, then 1.3 ml (9.6 mmol) of phenyl chlorothionoformate are added and the medium is stirred at −78° C. for 1 hour and then at ambient temperature for 1 hour 30 min. After evaporation of the tetrahydrofuran, the reaction medium is extracted with dichloromethane and washed with water. The organic phase is separated by settling, dried over magnesium sulfate, filtered and evaporated under vacuum. The 9 g (8.7 mmol) of residue obtained are placed in 100 ml of toluene and 71 mg (0.4 mmol) of 2,2'-azobis(2-methylpropionitrile) and then 3.5 ml (13.1 mmol) of tributyltin hydride are added. The reaction medium is heated at 110° C. for 20 minutes. After addition of water, the reaction medium is extracted with ethyl acetate. The organic phase is washed with water and with a saturated aqueous sodium chloride solution, dried over magnesium sulfate, filtered and evaporated. The residue obtained is purified by chromatography on a silica column eluted with a mixture of heptane and ethyl acetate (90/10) and then increase in the polarity up to a 70/30 heptane/ethyl acetate mixture. After evaporation of the solvents, 2.85 g of tert-butyl (S)-{4'-[3-(4-benzyl-2-oxooxazolidin-3-yl)-2-ethoxy-3-oxopropyl] biphenyl-3-yl}methylcarbamate are obtained. Yield=60%.

f) Preparation of 4(S)-Benzyl-3-[2(S)-ethoxy-3-(3'-(methylamino)biphenyl-4-yl)propionyl]oxazolidin-2-one:

9 ml (114 mmol) of trifluoroacetic acid are added dropwise to a solution of 8.5 g (15.2 mmol) of (S)-{4'-[3-(4-benzyl-2-oxooxazolidin-3-yl)-2-ethoxy-3-oxopropyl]biphenyl-3-yl}methylcarbamate in 150 ml of dichloromethane. The reaction medium is stirred at ambient temperature for 24 h, added to water and extracted with dichloromethane. The organic phase is dried over magnesium sulfate, filtered and evaporated. 8.7 g of 4(S)-benzyl-3-[2(S)-ethoxy-3-(3'-(methylamino)biphenyl-4-yl)propionyl]oxazolidin-2-one are obtained in the form of a trifluoroacetate salt. Yield=100%.

g) Preparation of 1-{4'-[3-(4(S)-Benzyl-2-oxooxazolidin-3-yl)-2(S)-ethoxy-3-oxopropyl]biphenyl-3-yl}-3-heptyl-1-methylurea:

1.1 ml (7.7 mmol) of triethylamine and then 2.25 ml (14.0 mmol) of heptyl isocyanate are added dropwise to a solution of 4 g (7.0 mmol) of 4(S)-benzyl-3-[2(S)-ethoxy-3-(3'-(methylamino)biphenyl-4-yl)propionyl]oxazolidin-2-one in 50 ml of dichloromethane. After stirring at ambient temperature for 20 hours, the reaction medium is placed in water and extracted with dichloromethane. The organic phase is dried over magnesium sulfate, filtered and evaporated. The residue obtained is purified by chromatography on a silica column eluted with a mixture of heptane and ethyl acetate (50/50). After evaporation of the solvents, 3.6 g of 1-{4'-[3-(4(S)-benzyl-2-oxooxazolidin-3-yl)-2(S)-ethoxy-3-oxopropyl]biphenyl-3-yl}-3-heptyl-1-methylurea are collected in the form of a colorless oil. Yield=86%.

h) Synthesis of 2(S)-Ethoxy-3-[3'-(3-heptyl-1-methylureido)biphenyl-4-yl]propanoic acid:

18 ml (9.0 mmol) of a 0.5M aqueous lithium hydroxide solution are added to a solution, cooled beforehand to 0° C., of 3.6 g (6.0 mmol) of 1-{4'-[3-(4(S)-benzyl-2-oxooxazolidin-3-yl)-2(S)-ethoxy-3-oxopropyl]biphenyl-3-yl}-3-heptyl-1-methylurea in 80 ml of tetrahydrofuran. The reaction medium is stirred at 0° C. for 2 hours, then a portion of the tetrahydrofuran is evaporated, and water and n-butanol are added. The reaction medium is acidified with a 1N hydrochloric acid solution to pH 3 and extracted with n-butanol. The organic phase is dried over magnesium sulfate, filtered and evaporated under vacuum. The residue obtained is purified by chromatography on a silica column eluted with a mixture of heptane and ethyl acetate (70/30) and then increase in the polarity up to a 50/50 heptane/ethyl acetate mixture. After evaporation of the solvents, 1.5 g of 2(S)-ethoxy-3-[3'-(3-heptyl-1-methylureido)biphenyl-4-yl]propanoic acid are collected in the form of a colorless oil. Yield=57%.

$^1$H NMR (δ, CDCl$_3$): 0.87 (t, J=7 Hz, 3H); 1.20-1.24 (m, 8H), 1.43 (m, 2H), 3.12 (m, 1H), 3.18 (m, 1H), 3.22 (m, 2H), 3.32 (s, 3H), 3.49 (m, 1H), 3.69 (m, 1H), 4.15 (m, 1H), 4.43 (m, 1H), 7.22-7.56 (m, 8H).

i) Preparation of L-Arginine salt of 2(S)-ethoxy-3-[3'-(3-heptyl-1-methylureido)biphenyl-4-yl]propanoic acid:

An aqueous solution of 0.4 g (2.3 mmol) of L-arginine is added dropwise to a solution, heated beforehand to 78° C., of 1 g (2.3 mmol) of 2(S)-ethoxy-3-[3'-(3-heptyl-1-methylureido)biphenyl-4-yl]propanoic acid in 22 ml of ethanol. The reaction medium is heated at 78° C. for 1 hour, then it is brought back to ambient temperature overnight and evaporated to dryness under vacuum. The residue obtained is taken up in 15 ml of ethyl ether, stirred at ambient temperature for 30 min and filtered off. The solid obtained is rinsed with ethyl ether and dried under vacuum in an oven. 1.3 g of the L-arginine salt of 2(S)-ethoxy-3-[3'-(3-heptyl-1-methylureido)biphenyl-4-yl]propanoic acid are obtained in the form of a white powder. Yield=100%.

$^1$H NMR (δ, d$_6$-DMSO): 0.84 (m, 3H), 1.00 (m, 3H), 1.22 (m, 8H), 1.37 (m, 2H), 1.27-1.39 (m, 4H), 2.90 (m, 1H), 2.97-3.07 (m, 3H), 3.18 (s, 3H), 3.20 (m, 1H), 3.60 (m, 1H), 3.67 (m, 1H), 6.05 (m, 1H), 7.18-7.54 (m, 8H).

EXAMPLE 2

Synthesis of 2(S)-Ethoxy-3-[3'-(1-methyl-3-pentylureido)biphenyl-4-yl]propanoic acid a) Preparation of 1-{4'-[3-(4(S)-Benzyl-2-oxooxazolidin-3-yl)-2(S)-ethoxy-3-oxopropyl]biphenyl-3-yl}-1-methyl-3-pentylurea:

In a manner analogous to Example 1 g), from 0.8 g (1.4 mmol) of 4(S)-benzyl-3-[2(S)-ethoxy-3-(3'-(methylamino)biphenyl-4-yl)propionyl]oxazolidin-2-one and 0.35 ml (2.8 mmol) of pentyl isocyanate, 0.54 g of 1-{4'-[3-(4(S)-benzyl-2-oxooxazolidin-3-yl)-2(S)-ethoxy-3-oxopropyl]biphenyl-3-yl}-1-methyl-3-pentylurea is obtained in the form of a colorless oil. Yield=67%.

b) Synthesis of 2(S)-Ethoxy-3-[3'-(1-methyl-3-pentylureido)biphenyl-4-yl]propanoic acid:

In a manner analogous to Example 1 h), from 0.53 g (0.93 mmol) of 1-{4'-[3-(4(S)-benzyl-2-oxooxazolidin-3-yl)-2(S)-ethoxy-3-oxopropyl]biphenyl-3-yl}-1-methyl-3-pentylurea and 2.8 ml (1.4 mmol) of a 0.5N aqueous sodium hydroxide solution, 0.32 g of 2(S)-ethoxy-3-[3'-(1-methyl-3-pentylureido)biphenyl-4-yl]propanoic acid is obtained in the form of a colorless oil. Yield=84%.

$^1$H NMR (δ, CDCl$_3$): 0.87 (t, J=7 Hz, 3H), 1.21 (t, J=7 Hz, 3H), 1.25-1.37 (m, 8H), 1.60 (m, 2H), 3.11 (dd, J=7.8 Hz, J=14 Hz, 1H), 3.38 (dd, J=7 Hz, J=14 Hz, 1H), 3.40 (m, 2H), 3.47 (m, 3H), 3.50 (m, 1H), 3.65 (m, 1H), 4.15 (m, 1H), 6.94 (d, J=8.4 Hz, 1H), 7.35-7.40 (m, 3H), 7.75-7.82 (m, 3H).

c) Preparation of L-Arginine salt of 2(S)-ethoxy-3-[3'-(1-methyl-3-pentylureido)biphenyl-4-yl]propanoic acid:

In a manner analogous to Example 1i), from 0.32 g (0.8 mmol) of 2(S)-ethoxy-3-[3'-(1-methyl-3-pentylureido)biphenyl-4-yl]propanoic acid and 0.13 g (0.8 mmol) of arginine, 0.45 g of the L-arginine salt of 2(S)-ethoxy-3-[3'-(1-methyl-3-pentylureido)biphenyl-4-yl]propanoic acid is obtained in the form of a white solid. Yield=100%.

$^1$H NMR (δ, d$_6$-DMSO): 0.86 (t, J=7 Hz, 3H), 1.01 (t, J=7 Hz, 3H), 1.20-1.28 (m, 8H), 1.30 (m, 2H), 1.40 (m, 2H), 1.41-1.57 (m, 2H), 2.8 (m, 1H), 3.00-3.10 (m, 4H), 3.20 (s, 3H), 3.22 (m, 1H), 3.33 (m, 1H), 3.42 (m, 1H), 3.67 (m, 1H), 6.06 (m, 1H), 7.19-7.55 (m, 8H).

EXAMPLE 3

Synthesis of 2(S)-Cyclopropylmethoxy-3-[3'-(3-heptyl-1-methylureido)biphenyl-4-yl]propanoic acid a) 3.6 g (12.7 mmol) of tert-butyl (3-bromophenyl)-N-methylcarbamate, prepared in a manner analogous to Example 1b), are dissolved in 15 ml of dichloromethane. 5 ml of trifluoroacetic acid are added and the reaction mixture is stirred at ambient temperature for 1 hour. The reaction is halted by the addition of 50 ml of a saturated sodium hydrogencarbonate solution and then extraction is carried out with ethyl acetate. The organic phases are combined and dried over sodium sulfate. The solvents are evaporated and then the residue is chromatographed on silica gel (heptane/ethyl acetate 50/50). 2.14 g of 3-bromo-N-methylaniline are obtained in the form of an oil. Yield=90%.

b) 890 mg (3.5 mmol) of pinacolborane are added to a mixture of 600 mg (3.2 mmol) of 3-bromo-N-methylaniline and 1 g (10.2 mmol) of potassium acetate in the presence of 130 mg (0.16 mmol, 5 mol %) of palladium dichloride diphenylphosphinopropane ferrocene (PdCl$_2$dppf) in 10 ml of dimethylformamide. The mixture is stirred at 90° C. for 2 hours. The reaction is halted by the addition of 20 ml of water and then extraction is carried out with ethyl acetate. The organic phases are combined and dried over sodium sulfate. The solvents are evaporated and then the residue is chromatographed on silica gel (heptane/ethyl acetate 80/20). 420 mg of methyl[3-(4,4,5,5-tetramethyl-1,3,2-dioxaborolan-2-yl)phenyl]amine are obtained in the form of an oil. Yield=57%.

c) 72 ml (0.122 mol, 2.5 eq) of tert-butyllithium (1.7M/pentane) are added slowly using a needle to a suspension of 35 g (0.148 mol, 3 eq) of 1,4-dibromobenzene in 100 ml of tert-butyl methyl ether at −30° C. The mixture is stirred at −30° C. for 10 min and then 5.3 g (0.059 mol) of copper(I) cyanide are introduced into the above solution. The reaction mixture is stirred at −30° C. for 20 min. A solution of 5 g (0.049 mol) of methyl (S)-glycidate in 10 ml of tert-butyl methyl ether is added while keeping the temperature below −20° C. The mixture is stirred at −30° C. for 20 min and then the reaction is halted by the addition of a saturated ammonium chloride solution. The mixture is extracted with 3×300 ml of ethyl acetate. The organic phases are combined and dried over sodium sulfate. The solvents are evaporated and then the residue is chromatographed on silica gel (heptane 100% up to heptane/ethyl acetate 60/40). 7.2 g of methyl (S)-3-(4-bromophenyl)-2-hydroxypropionate are obtained in the form of a solid. Yield=56%.

d) 0.11 ml (1.15 mmol) of bromomethylcyclopropane are added to a mixture of 267 mg (3.48 mmol) of silver oxide and 100 mg (0.38 mmol) of methyl (S)-3-(4-bromophenyl)-2-hydroxypropionate in 2 ml of diethyl ether. The reaction mixture is stirred at 50° C. for 24 hours. The mixture is filtered and then the solvents are evaporated. The residue is chromatographed on silica gel (heptane/ethyl acetate 85/15). 145 mg of methyl (S)-3-(4-bromophenyl)-2-(cyclopropylmethoxy)propanoate are obtained in the form of an oil. Yield=50%.

e) 53 mg (0.046 mmol) of tetrakis(triphenylphosphine) palladium are added to a solution of 145 mg (0.46 mmol) of methyl (S)-3-(4-bromophenyl)-2-(cyclopropylmethoxy)propionate and 129 mg (0.55 mmol) of methyl[3-(4,4,5,5-tetramethyl-1,3,2-dioxaborolan-2-yl)phenyl]amine in 3 ml of dimethylformamide. 0.3 ml of a 2M potassium phosphate solution is added and the reaction mixture is stirred at 90° C. for 2 hours. The reaction is halted by the addition of 10 ml of water and then extraction is carried out with ethyl acetate. The organic phases are combined and dried over sodium sulfate. The solvents are evaporated and then the residue is chromatographed on silica gel (heptane/ethyl acetate 80/20). 70 mg of methyl (S)-2-cyclopropylmethoxy-3-[3'-(methylamino)biphenyl-4-yl]propanoate are obtained in the form of an oil. Yield=45%.

f) 40 µl (0.25 mmol) of heptyl isocyanate are added to a solution of 70 g (0.2 mmol) of methyl (S)-2-cyclopropylmethoxy-3-[3'-(methylamino)biphenyl-4-yl]propionate in 2 ml of dichloromethane. The reaction mixture is stirred at ambient temperature for 48 hours. The reaction is halted by the addition of 2 ml of water and then extraction is carried out with ethyl acetate. The organic phases are combined and dried over sodium sulfate. The solvents are evaporated and then the residue is chromatographed on silica gel (heptane/ethyl acetate 70/30). 86 mg of methyl (S)-2-cyclopropylmethoxy-3-[3'-(3-heptyl-1-methylureido)biphenyl-4-yl]propanoate are obtained in the form of an oil. Yield=87%.

g) 21 mg (0.54 mmol) of sodium hydroxide are added to a solution of 86 mg (0.18 mmol) of methyl (S)-2-cyclopropylmethoxy-3-[3'-(3-heptyl-1-methylureido)biphenyl-4-yl]propionate in 2 ml of 9/1 tetrahydrofuran/methanol. The reaction mixture is stirred at ambient temperature overnight. The reaction is halted by the addition of 2 ml of water and 0.5 ml of acetic acid, and then extraction is carried out with ethyl acetate. The organic phases are combined and dried over sodium sulfate. The solvents are evaporated and then the residue is chromatographed on silica gel (dichloromethane/methanol 90/10). 70 mg of 2(S)-cyclopropylmethoxy-3-[3'-(3-heptyl-1-methylureido)biphenyl-4-yl]propanoic acid are obtained in the form of an oil. Yield=84%.

$^1$H NMR: (CDCl$_3$, 400 MHz): 0.20 (m, 2H), 0.56 (m, 2H), 0.86 (t, J=6.8 Hz, 3H), 1.05 (m, 1H), 1.24 (m, 8H), 1.42 (m, 2H), 3.07-3.25 (m, 4H), 3.32 (s, 3H), 3.39 (m, 2H), 4.20 (dd, J=4, 7.6 Hz, 1H), 4.40 (t, J=5.6 Hz, 1H), 7.22 (d, J=7.6 Hz, 1H), 7.38 (d, J=8.4 Hz, 2H), 7.47-7.54 (m, 5H).

EXAMPLE 4

Synthesis of 2-(S)-Propyloxy-3-[3'-(3-heptyl-1-methylureido)biphenyl-4-yl]propanoic acid a) 0.22 ml (2.31 mmol) of propyl iodide is added to a mixture of 793 mg (3.48 mmol) of silver oxide and 300 mg (1.16 mmol) of methyl (S)-3-(4-bromophenyl)-2-hydroxypropionate in 3 ml of diethyl ether. The reaction mixture is stirred at 50° C. for 12 hours. The mixture is filtered and then the solvents are evaporated. The residue is chromatographed on silica gel (heptane/ethyl acetate 80/20). 291 mg of methyl (S)-3-(4-bromophenyl)-2-(propyloxy)propanoate are obtained in the form of an oil. Yield=83%.

b) 38 mg (0.033 mmol) of tetrakis(triphenylphosphine) palladium are added to a solution of 100 mg (0.33 mmol) of methyl (S)-3-(4-bromophenyl)-2-(propyloxy)propionate and 90 mg (0.39 mmol) of methyl[3-(4,4,5,5-tetramethyl-1,3,2-dioxaborolan-2-yl)phenyl]amine in 1 ml of dimethylformamide. 0.2 ml of a 2M potassium phosphate solution is added and the reaction mixture is stirred at 90° C. for 2 hours. The reaction is halted by the addition of 10 ml of water and then extraction is carried out with ethyl acetate. The organic phases are combined and dried over sodium sulfate. The solvents are evaporated and then the residue is chromatographed on silica gel (heptane/ethyl acetate 80/20). 76 mg of methyl (S)-2-propyloxy-3-[3'-(methylamino)biphenyl-4-yl]propanoate are obtained in the form of an oil. Yield=70%.

c) 156 µl (0.96 mmol) of heptyl isocyanate are added to a solution of 210 mg (0.64 mmol) of methyl (S)-2-propyloxy-3-[3'-(methylamino)biphenyl-4-yl]propanoate in 3 ml of dichloromethane. The reaction mixture is stirred at ambient temperature for 48 hours. The reaction is halted by the addition of 2 ml of water and then extraction is carried out with ethyl acetate. The organic phases are combined and dried over sodium sulfate. The solvents are evaporated and then the residue is chromatographed on silica gel (heptane/ethyl acetate 70/30). 200 mg of methyl (S)-2-propyloxy-3-[3'-(3-heptyl-1-methylureido)biphenyl-4-yl]propanoate are obtained in the form of an oil. Yield=66%.

d) 51 mg (1.28 mmol) of sodium hydroxide are added to a solution of 200 mg (0.42 mmol) of methyl (S)-2-propyloxy-3-[3'-(3-heptyl-1-methylureido)biphenyl-4-yl]propanoate in 2 ml of 9/1 tetrahydrofuran/methanol. The reaction mixture is stirred overnight at ambient temperature. The reaction is halted by the addition of 2 ml of water and 0.5 ml of acetic acid, and then extraction is carried out with ethyl acetate. The organic phases are combined and dried over sodium sulfate. The solvents are evaporated and then the residue is chromatographed on silica gel (dichloromethane/methanol 90/10). 147 mg of 2-(S)-propyloxy-3-[3'-(3-heptyl-1-methylureido)biphenyl-4-yl]propanoic acid are obtained in the form of an oil. Yield=76%.

$^1$H NMR (CDCl$_3$, 400 MHz): 0.86 (t, J=7.1 Hz, 3H), 0.90 (t, J=7.2 Hz, 3H), 1.24 (m, 8H), 1.43 (m, 2H), 1.61 (sext, J=7 Hz, 2H), 3.07-3.22 (m, 4H), 3.32 (s, 3H), 3.38 and 3.57 (2q, J=7.7 Hz, 2H), 4.13 (m, 1H), 4.41 (t, J=5.6 Hz, 1H), 7.22 (d, J=7.6 Hz, 1H), 7.37 (d, J=8.4 Hz, 2H), 7.47-7.55 (m, 5H).

EXAMPLE 5

Synthesis of 2(S)-Benzyloxy-3-[3'-(3-heptyl-1-methylureido)biphenyl-4-yl]propanoic acid a) 1.9 ml (16 mmol) of benzyl bromide are added to a mixture of 4.4 g (19 mmol) of silver oxide and 3.5 g (13 mmol) of methyl (S)-3-(4 4-bromophenyl)-2-hydroxypropionate in 20 ml of diethyl ether. The reaction mixture is stirred at 50° C. for 12 hours. The mixture is filtered and then the solvents are evaporated. The residue is chromatographed on silica gel (heptane/ethyl acetate 80/20). 4 g of methyl (S)-3-(4-bromophenyl)-2-benzyloxypropanoate are obtained in the form of an oil. Yield=85%.

b) 635 mg (0.55 mmol) of tetrakis(triphenylphosphine) palladium are added to a solution of 4 g (11 mmol) of methyl (S)-3-(4-bromophenyl)-2-benzyloxypropionate and 4 g (17 mmol) of methyl[3-(4,4,5,5-tetramethyl-1,3,2-dioxaborolan-2-yl)phenyl]amine in 25 ml of dimethylformamide. 10 ml of a 2M potassium phosphate solution are added and the reaction mixture is stirred at 70° C. for 1 hour. The reaction is halted by the addition of 50 ml of water and then extraction is carried out with ethyl acetate. The organic phases are combined and dried over sodium sulfate. The solvents are evaporated and then the residue is chromatographed on silica gel (heptane/ethyl acetate 80/20). 2.6 g of methyl (S)-2-benzyloxy-3-[3'-(methylamino)biphenyl-4-yl]propanoate are obtained in the form of an oil. Yield=61%.

c) 2.25 ml (13.9 mmol) of heptyl isocyanate are added to a solution of 2.6 g (6.95 mmol) of methyl (S)-2-benzyloxy-3-[3'-(methylamino)biphenyl-4-yl]propanoate in 15 ml of dichloromethane. The reaction mixture is stirred at ambient temperature for 20 hours. The reaction is halted by the addition of 20 ml of water and then extraction is carried out with ethyl acetate. The organic phases are combined and dried over sodium sulfate. The solvents are evaporated and then the residue is chromatographed on silica gel (heptane/ethyl acetate 70/30). 2.42 g of methyl (S)-2-benzyloxy-3-[3'-(3-heptyl-1-methylureido)biphenyl-4-yl]propanoate are obtained in the form of an oil. Yield=67%.

d) 16 mg (0.4 mmol) of sodium hydroxide are added to a solution of 70 mg (0.42 mmol) of methyl (S)-2-benzyloxy-3-[3'-(3-heptyl-1-methylureido)biphenyl-4-yl]propanoate in 2 ml of 9/1 tetrahydrofuran/methanol. The reaction mixture is stirred overnight at ambient temperature. The reaction is halted by the addition of 2 ml of water and 0.5 ml of acetic acid, and then extraction is carried out with ethyl acetate. The organic phases are combined and dried over sodium sulfate. The solvents are evaporated and then the residue is chromatographed on silica gel (dichloromethane/methanol 90/10). 49 mg of 2(S)-benzyloxy-3-[3'-(3-heptyl-1-methylureido)biphenyl-4-yl]propanoic acid are obtained in the form of an oil. Yield=72%.

$^1$H NMR (CDCl$_3$, 400 MHz): 0.86 (t, J=7 Hz, 3H), 1.24 (m, 8H), 1.43 (m, 2H), 1.61 (sext, J=7 Hz, 2H), 3.10-3.26 (m, 4H), 3.33 (s, 3H), 4.24 (dd, J=4.4, 8 Hz, 1H), 4.44 (t, J=5.6 Hz, 1H), 4.48 and 4.73 (2d, J=11.6 Hz, 2H), 7.21-7.30 (m, 6H), 7.37 (d, J=8.4 Hz, 2H), 7.47-7.55 (m, 5H).

EXAMPLE 6

Synthesis of 2(S)-Allyloxy-3-[3'-(3-heptyl-1-methylureido)biphenyl-4-yl]propanoic acid a) 100 mg of 10% palladium-on-charcoal are added to a solution of 2.4 g (4.66 mmol) of methyl (S)-2-benzyloxy-3-[3'-(3-heptyl-1-methylureido)biphenyl-4-yl]propanoate in 10 ml of methanol. The reaction mixture is stirred overnight under a hydrogen atmosphere. The reaction mixture is filtered and then the solvents are evaporated. The residue is filtered through silica gel (ethyl acetate). 1.61 g of methyl (S)-3-[3'-(3-heptyl-1-methylureido)biphenyl-4-yl]-2-hydroxypropionate are collected in the form of a colorless oil. Yield=81%.

b) 58 µl (0.70 mmol) of allyl bromide are added to a mixture of 162 mg (0.70 mmol) of silver oxide and 200 mg (0.47 mmol) of methyl (S)-3-[3'-(3-heptyl-1-methylureido)biphenyl-4-yl]-2-hydroxypropanoate in 3 ml of diethyl ether. The reaction mixture is stirred at 40° C. for 24 hours. The mixture is filtered and then the solvents are evaporated. The residue is chromatographed on silica gel (heptane/ethyl acetate 80/20 up to 60/40). 180 mg of methyl (S)-2-allyloxy-3-[3'-(3-heptyl-1-methylureido)biphenyl-4-yl]propanoate are obtained in the form of an oil. Yield=82%.

c) 56 mg (1.4 mmol, 3 eq) of sodium hydroxide are added to a solution of 200 mg (0.47 mmol, 1 eq) of methyl (S)-2-allyloxy-3-[3'-(3-heptyl-1-methylureido)biphenyl-4-yl]propanoate in 2 ml of 9/1 THF/methanol. The reaction mixture is stirred at ambient temperature for 3 hours. The reaction is halted by the addition of 2 ml of water and 0.5 ml of acetic acid, and then extraction is carried out with ethyl acetate. The organic phases are combined and dried over sodium sulfate. The solvents are evaporated and then the residue is chromatographed on silica gel (dichloromethane/methanol 90/10). 152 mg of 2(S)-allyloxy-3-[3'-(3-heptyl-1-methylureido)biphenyl-4-yl]propanoic acid are obtained in the form of an oil. Yield=78%.

$^1$H NMR (CDCl$_3$, 400 MHz): 0.86 (t, J=6.8 Hz, 3H), 1.26 (m, 8H), 1.42 (m, 2H), 3.09-3.25 (m, 4H), 3.32 (s, 3H), 4.01 (dd, J=5.8, 12.6 Hz, 1H), 4.16 (dd, J=5.7, 12.6 Hz, 1H), 4.22 (dd, J=4.3, 7.6 Hz, 1H), 4.41 (t, J=5.6 Hz, 1H), 5.22 (d, J=10.4 Hz, 1H), 5.25 (d, J=18.8 Hz, 1H), 5.83 (m, 1H), 7.22 (d, J=7.6 Hz, 1H), 7.37 (d, J=8.4 Hz, 2H), 7.52 (m, 5H).

EXAMPLE 7

Crossed-Curve PPAR Transactivation Assay

Activation of the PPAR receptors by an agonist (activator) in HeLN cells leads to the expression of a reporter gene, luciferase, which, in the presence of a substrate, generates light. The modulation of the PPAR receptors is measured by quantifying the luminescence produced after incubation of the cells in the presence of a reference agonist. The ligands will displace the agonist from its site. The measurement of the activity is performed by quantifying the light produced. This measurement makes it possible to determine the modulatory activity of the compounds according to the invention by the determination of the constant which is the affinity of the molecule for the PPAR receptor. Since this value can fluctuate depending on the basal activity and the expression of the receptor, it is referred to as apparent Kd (KdApp in nM).

To determine this constant, "crossed curves" for the test product, against a reference agonist, are prepared using a 96-well plate: 10 concentrations of the test product plus a concentration 0 are arranged in a line, and 7 concentrations of the agonist plus a concentration 0 are arranged in a column. This is 88 measurement points for 1 product and 1 receptor. The remaining 8 wells are used for repeatability controls.

In each well, the cells are in contact with a concentration of the test product and a concentration of the reference agonist, 2-(4-{2-[3-(2,4-difluorophenyl)-1-heptylureido]ethyl}phenylsulfanyl)-2-methylpropionic acid for PPARα, {2-methyl-4-[4-methyl-2-(4-(trifluoromethyl)phenyl)thiazol-5-ylmethylsulfanyl]phenoxy}acetic acid for PPARδ and 5-{4-[2-(methyl(pyrid-2-yl)amino)ethoxy]benzyl}thiazolidine-2,4-dione for PPARγ. Measurements are also taken for total agonist controls with the same products.

The HeLN cell lines used are stable transfectants containing the plasmids ERE-βGlob-Luc-SV-Neo (reporter gene) and PPAR (α, δ, γ) Gal-hPPAR. These cells are seeded in 96-well plates at the rate of 10 000 cells per well in 100 µl of DMEM medium without phenol red and supplemented with 10% of defatted calf serum. The plates are then incubated for 16 hours at 37° C. and 7% CO$_2$.

The various dilutions of the test products and of the reference ligand are added at the rate of 5 µl per well. The plates are subsequently incubated for 18 hours at 37° C. and 7% CO$_2$. The culture medium is removed by turning over and 100 µl of a 1:1 PBS/luciferin mixture are added to each well. After 5 minutes, the plates are read using the luminescence reader.

These crossed curves make it possible to determine the AC50 values (concentration at which 50% activation is observed) of the reference ligand at various concentrations of test product. These AC50 values are used to calculate the Schild regression by plotting a straight line corresponding to the Schild equation ("Quantitation in Receptor Pharmacology", Terry P. Kenakin, *Receptors and Channels*, 2001, 7, 371-385) which allows the KdApp values (in nM) to be obtained.

Transactivation Results:

| Compounds | PPARα KdApp (in nM) | PPARδ KdApp (in nM) | PPARγ KdApp (in nm) |
|---|---|---|---|
| Reference 1: 2-(4-{2-[3-(2,4-difluorophenyl)-1-heptylureido]ethyl}phenylsulfany)-2-methyl propionic acid | 200 | n.a. | n.a. |
| Reference 2: {2-methyl-4-[4-methyl-2-(4-(trifluoromethyl)phenyl)thiazol-5-ylmethylsulfanyl]phenoxy}acetic acid | n.a. | 10 | n.a. |
| Reference 3: 5-{4-[2-(methyl(pyridin-2-yl)amino)ethoxy]benzyl}thiazolidine-2,4-dione | n.a. | n.a. | 30 |
| Example 1: 2(S)-ethoxy-3-[3'-(3-heptyl-1-methylureido)biphenyl-4-yl]propionic acid | 30 | 250 | <1 |
| Example 2: 2(S)-ethoxy-3-[3'-(1-methyl-3-penylureido)biphenyl-4-yl]propionic acid | 250 | 2000 | 0.03 |
| Example 4: 2-(S)-propyloxy-3-[3'-(3-heptyl-1-methylureido)biphenyl-4-yl]propionic acid | 30 | 500 | 0.025 |
| Example 5: 2-(S)-benzyloxy-3-[3'-(3-heptyl-1-methylureido)biphenyl-4-yl]propionic acid | 250 | n.a. | 0.03 |
| Example 6: 2-(S)-allyloxy-3-[3'-(3-heptyl-1-methylureido)biphenyl-4-yl]propionic acid | 2 | 50 | 0.003 | n.a. means not active

TABLE 1

| Compounds according to the present invention | Substituent as denoted in the present document | KdApp in nM | Compounds according to Patent FR 2 812 876 | Substituent as denoted in Patent FR 2 812 876 | KdApp in nM |
|---|---|---|---|---|---|
| Example 1 2(S)-Ethoxy-3-[3'-(3-heptyl-1-methylureido)biphenyl-4-yl]propionic acid | R1 = $CH_2CH_3$ | <1 | Example 13 (S)-2-Ethoxy-3-(3'-{[methyl(1-phenylmethanoyl)amino]methyl}biphenyl-4-yl)propionic acid | R10 = $CH_2CH_3$ | 500 |
| Example 2 2(S)-Ethoxy-3-[3'-(1-methyl-3-pentylureido)biphenyl-4-yl]propionic acid | R2 = $(CH_2)_4CH_3$ | 0.03 | Example 22 N-[4'-(2,4-Dioxothiazolidin-5-ylmethyl)biphenyl-3-ylmethyl]-2,2,N-trimethyl-propionamide | R4 = $C(CH_3)_3$ | 250 |
| Example 1 2(S)-Ethoxy-3-[3'-(3-heptyl-1-methylureido)biphenyl-4-yl]propionic acid | R2 = $(CH_2)_6CH_3$ | <1 | Example 35 N-[4'-(2,4-Dioxothiazolidin-5-ylmethyl)biphenyl-3-ylmethyl]-N-methylheptanamide | R4 = $(CH_2)_5CH_3$ | 1000 |
| Example 4 2(S)-propyloxy-3-[3'-(3-heptyl-1-methylureido)biphenyl-4-yl]propionic acid | R2 = $(CH_2)_6CH_3$ | 0.025 | Example 23 N-Octyl-4'-(2,4-dioxothiazolidin-5-ylmethyl)biphenyl-3-carboxamide | R4 = $(CH_2)_7CH_3$ | 2000 |
| Example 5 2(S)-benzyloxy-3-[3'-(3-heptyl-1- | R2 = $(CH_2)_6CH_3$ | 0.03 | Example 32 N-[4'-(2,4-Dioxothiazolidin-5- | R4 = $(CH_2)_8CH_3$ | 250 |

TABLE 1-continued

| Compounds according to the present invention 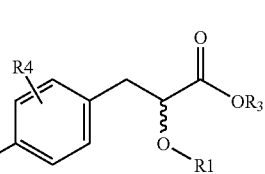 Substituent as denoted in the present document | KdApp in nM | Compounds according to Patent FR 2 812 876 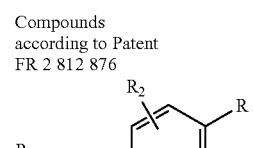 Substituent as denoted in Patent FR 2 812 876 | KdApp in nM |
|---|---|---|---|
| methylureido)biphenyl-4-yl]propionic acid | | ylmethyl)biphenyl-3-ylmethyl]-N-methyldecanamide | |

These results show the affinity of the compounds for PPARγ and more particularly the specificity of the affinity of the compounds of the invention for the PPARγ subtype, compared with the affinity of the compounds for the PPARα subtype or for the PPARδ subtype.

EXAMPLE 8

Compositions

Various specific formulations based on the compounds according to the invention are illustrated in this example.

A—Oral Route:

| (a) 0.2 g Tablet: | |
|---|---|
| Compound of Example 1 | 0.001 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |
| (b) Suspension to be taken orally in 5 ml vials: | |
| Compound of Example 5 | 0.001 g |
| Glycerol | 0.500 g |
| 70% Sorbitol | 0.500 g |
| Sodium saccharinate | 0.010 g |
| Methyl para-hydroxybenzoate | 0.040 g |
| Flavoring | q.s. |
| Purified water | q.s. for 5 ml |
| (c) 0.8 g Tablet: | |
| Compound of Example 2 | 0.500 g |
| Pregelatinized starch | 0.100 g |
| Microcrystalline cellulose | 0.115 g |
| Lactose | 0.075 g |
| Magnesium stearate | 0.010 g |
| (d) Suspension to be taken orally in 10 ml vials: | |
| Compound of Example 4 | 0.200 g |
| Glycerol | 1.000 g |
| 70% Sorbitol | 1.000 g |
| Sodium saccharinate | 0.010 g |
| Methyl para-hydroxybenzoate | 0.080 g |
| Flavoring | q.s. |
| Purified water | q.s. for 10 ml |

B—Topical Route:

| (a) Salve: | |
|---|---|
| Compound of Example 6 | 0.020 g |
| Isopropyl myristate | 81.700 g |
| Liquid petrolatum | 9.100 g |
| Silica ("Aerosil 200", marketed by Degussa) | 9.180 g |
| (b) Salve: | |
| Compound of Example 2 | 0.300 g |
| White petrolatum, pharmaceutical grade | q.s. for 100 g |
| (c) Nonionic water-in-oil cream: | |
| Compound of Example 1 | 0.100 g |
| Mixture of emulsive lanolin alcohols, of waxes and of oils ("Anhydrous eucerin", marketed by BDF) | 39.900 g |
| Methyl para-hydroxybenzoate | 0.075 g |
| Propyl para-hydroxybenzoate | 0.075 g |
| Sterile demineralized water | q.s. for 100 g |
| (d) Lotion: | |
| Compound of Example 3 | 0.100 g |
| Polyethylene glycol (PEG) 400 | 69.900 g |
| 95% Ethanol | 30.000 g |
| (e) Hydrophobic salve: | |
| Compound of Example 5 | 0.300 g |
| Isopropyl myristate | 36.400 g |
| Silicone oil ("Rhodorsil 47 V 300", marketed by Rhône-Poulenc) | 36.400 g |
| Beeswax | 13.600 g |
| Silicone oil ("Abil 300,000 cSt", marketed by Goldschmidt) | q.s. for 100 g |
| (f) Nonionic oil-in-water cream: | |
| Compound of Example 2 | 1.000 g |
| Cetyl alcohol | 4.000 g |
| Glyceryl monostearate | 2.500 g |
| PEG 50 stearate | 2.500 g |
| Shea butter | 9.200 g |

| | |
|---|---|
| Propylene glycol | 2.000 g |
| Methyl para-hydroxybenzoate | 0.075 g |
| Propyl para-hydroxybenzoate | 0.075 g |
| Sterile demineralized water | q.s. for 100 g |

Each patent, patent application, publication, text and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A biaromatic compound having the following structural formula (I):

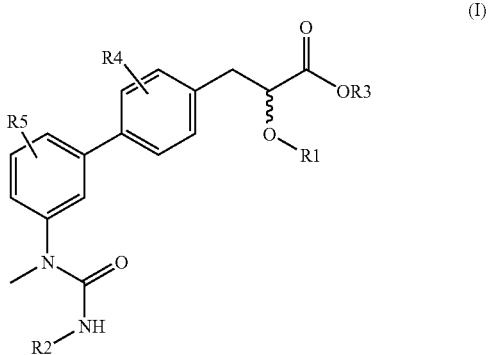

in which:
- R1 is an alkyl radical selected from the group consisting of methyl, ethyl, n-propyl, isopropyl, cyclopropyl, isobutyl, tert-butyl, n-pentyl, isopentyl, n-hexyl, isohexyl, cyclohexyl, ethylenyl, allyl, propenyl, butenyl, pentenyl and hexenyl, or an acetyl group or a methylcyclopropane group;
- R2 is an alkyl radical having 3 to 8 carbon atoms;
- R3 is a hydrogen atom or an alkyl radical having 1 to 6 carbon atoms;
- R4 and R5, which are identical or different, are each a hydrogen atom, a halogen atom, a hydroxyl radical, an alkyl radical having from 1 to 6 carbon atoms, an alkoxy radical, a benzyloxy radical or a trifluoromethyl radical;

or an isomer, optical or geometrical, pure or as a mixture, in any proportion, of said compound of formula (I) or a tautomeric form, or a salt of said compound of formula (I).

2. The biaromatic compound as defined by claim 1, comprising an alkali metal salt or an alkaline earth metal salt or an organic amine salt thereof.

3. A sodium salt of the biaromatic compound as defined by claim 1.

4. An amino acid salt of the biaromatic compound as defined by claim 1.

5. An arginine salt or a lysine salt of the biaromatic compound as defined by claim 1.

6. The biaromatic compound as defined by claim 1, wherein R2 is selected from the group consisting of n-propyl, isopropyl, cyclopropyl, n-butyl, isobutyl, tert-butyl, n-pentyl, isopentyl, cyclopentyl, n-hexyl, isohexyl, cyclohexyl, n-heptyl, isoheptyl, n-octyl, isooctyl, allyl, propenyl, butenyl, pentenyl, hexenyl, heptenyl and octenyl radicals.

7. The biaromatic compound as defined by claim 1, bearing a fluorine, bromine or chlorine atom substituent.

8. The biaromatic compound as defined by claim 1, bearing a methoxy, ethoxy, isopropyloxy, tert-butoxy, or hexyloxy radical substituent.

9. The biaromatic compound as defined by claim 1, selected from the group consisting of:
1. 2(S)-Ethoxy-3-[3'-(3-heptyl-1-methylureido)biphenyl-4-yl]propanoic acid,
2. 2(S)-Ethoxy-3-[3'-(1-methyl-3-pentylureido)biphenyl-4-yl]propanoic acid,
3. 2(S)-Cyclopropylmethoxy-3-[3'-(3-heptyl-1-methylureido)biphenyl-4-yl]propanoic acid,
4. 2(S)-Propyloxy-3-[3'-(3-heptyl-1-methylureido)biphenyl-4-yl]propanoic acid,
6. 2(S)-Allyloxy-3-[3'-(3-heptyl-1-methylureido)biphenyl-4-yl]propanoic acid,
7. 2(S)-Cyclopropylmethoxy-3-[3'-(1-methyl-3-pentylureido)biphenyl-4-yl]propanoic acid,
8. 3-[3'-(1-Methyl-3-pentylureido)biphenyl-4-yl]-2(S)-propoxypropanoic acid,
9. 2(S)-Allyloxy-3-[3'-(1-methyl-3-pentylureido)biphenyl-4-yl]propanoic acid,
11. 2(S)-Methoxy-3-[3'-(1-methyl-3-pentylureido)biphenyl-4-yl]propanoic acid,
12. 3-[3'-(3-Heptyl-1-methylureido)biphenyl-4-yl]-2(S)-methoxypropanoic acid,
13. 2(S)-Ethoxy-3-[3'-(1-methyl-3-propylureido)biphenyl-4-yl]propanoic acid,
14. 3-[3'-(3-Cyclopropylmethyl-1-methylureido)biphenyl-4-yl]-2(S)-ethoxypropanoic acid,
15. 3-[3'-(3-Cyclopentylmethyl-1-methylureido)biphenyl-4-yl]-2(S)-ethoxypropanoic acid,
16. 2(S)-Ethoxy-3-[3-fluoro-3'-(1-methyl-3-pentylureido)biphenyl-4-yl]propanoic acid
17. 2(S)-Ethoxy-3-[4'-fluoro-3'-(1-methyl-3-pentylureido)biphenyl-4-yl]propanoic acid
18. 3-[3,4'-Difluoro-3'-(1-methyl-3-pentylureido)biphenyl-4-yl]-2(S)-ethoxypropanoic acid,
19. Methyl 2(S)-ethoxy-3-[3'-(3-heptyl-1-ethylureido)biphenyl-4-yl]propanoate,
20. Methyl 2(S)-cyclopropylmethoxy-3-[3'-(1-methyl-3-pentylureido)biphenyl-4-yl]propanoate,
21. 2(S)-Cyclopropylmethoxy-3-[3'-(3-cyclopropylmethyl-1-methylureido)biphenyl-4-yl]propanoic acid,
22. 3-{3'-[3-(2-Cyclohexylethyl)-1-methylureido]biphenyl-4-yl}-2(S)-ethoxypropanoic acid,
23. 2(R)-Ethoxy-3-[3'-(1-methyl-3-pentylureido)biphenyl-4-yl]propanoic acid,
24. 2(R)-Ethoxy-3-[3'-(3-heptyl-1-methylureido)biphenyl-4-yl]propanoic acid,
25. 2-Ethoxy-3-[3'-(3-heptyl-1-methylureido)biphenyl-4-yl]propanoic acid,
26. 2(R)-Allyloxy-3[3'-(3-heptyl-1-methylureido)biphenyl-4-yl]propanoic acid,
27. 3-[3'-(3-Allyl-1-methylureido)biphenyl-4-yl]-2(S)-ethoxypropanoic acid, and
28. Allyl 3-[3'-(3-allyl-1-methylureido)biphenyl-4-yl]-2(S)-ethoxypropanoate.

10. The biaromatic compound as defined by claim 1, having at least one of the following characteristics:
- R1 is a methyl, ethyl, n-propyl, isopropyl, cyclopropyl, isobutyl or tert-butyl radical, or a methylcyclopropane group, R2 is a n-pentyl, isopentyl, cyclopentyl, n-hexyl, isohexyl, cyclohexyl, n-heptyl or isoheptyl radical, R3 is a hydrogen atom, R4 and/or R5 are each a hydrogen atom or a fluorine atom.

11. A cosmetic composition comprising at least one biaromatic compound as defined by claim 1, formulated into a physiologically acceptable medium therefor.

12. The cosmetic composition as defined by claim 11, comprising from 0.001% to 3% by weight of said at least one biaromatic compound.

13. A pharmaceutical composition useful for regulating and/or restoring the metabolism of skin lipids, comprising a thus effective amount of at least one biaromatic compound as defined by claim 1, formulated into a physiologically acceptable medium therefor.

14. A cosmetic composition useful for body and/or hair hygiene, comprising a thus effective amount of at least one biaromatic compound as defined by claim 1, formulated into a cosmetically acceptable medium therefor.

15. The pharmaceutical composition as defined by claim 13, comprising from 0.001% to 10% by weight of said at least one biaromatic compound.

16. The pharmaceutical composition as defined by claim 13, comprising from 0.01% to 1% by weight of said at least one biaromatic compound.

17. A process for the synthesis of a compound of formula (I) or of an isomer, optical or geometrical, pure or as a mixture, in any proportion, of said compound of formula (I), of the tautomeric form, or of a salt of said compound of formula (I) as defined in claim 1, comprising the following stages:

a) Preparation of the compound of formula 1:

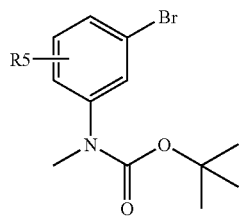

1 where R5 is a hydrogen atom, a halogen atom, a hydroxyl radical, an alkyl radical having from 1 to 6 carbon atoms, an alkoxy radical, a benzyloxy radical or a trifluoromethyl radical, from 3-bromoaniline, by protecting the amine with di(tert-butyl) dicarbonate and by then carrying out a methylation in the presence of sodium hydride;

b) Preparation of compound 2:

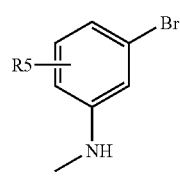

2 with R5 as defined above,
by treating compound 1 with an acid;

c) Preparation of compound 3:

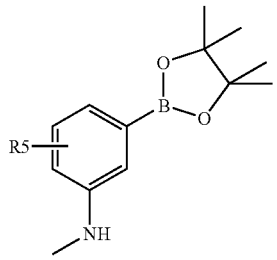

3 with R5 as defined above,
by the reaction of compound 2 with pinacolborane in the presence of a catalyst;

d) Preparation of compound 5:

5 with R4 representing a hydrogen atom, a halogen atom, a hydroxyl radical, an alkyl radical having from 1 to 6 carbon atoms, an alkoxy radical, a benzyloxy radical or a trifluoromethyl radical, by treating the epoxide 4

4 with an aryl cuprate;

e) Preparation of compound 6:

6 with R1 representing an alkyl group having from 1 to 6 carbon atoms, an acetyl group, a methylcyclopropane group, an aralkyl group or an aryl group and R4 as defined above;

by reacting compound 5 with an alkyl halide in the presence of silver oxide;

f) Preparation of compound 7:

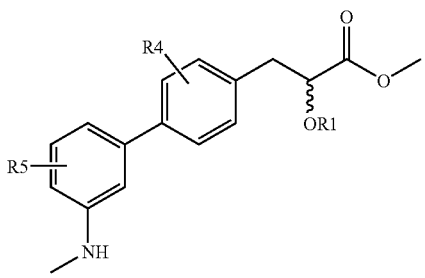

with R1, R4 and R5 as defined above, by the coupling of compound 6 and compound 3 according to a reaction of Suzuki type in the presence of tetrakis(triphenylphosphine)palladium;

g) Preparation of compound 8:

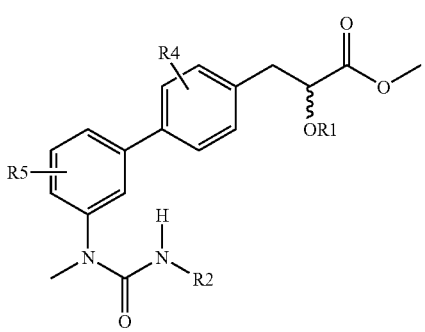

with R2 representing an alkyl group having from 3 to 8 carbon atoms and R1, R4 and R5 as defined above, by the reaction from compound 7 and an alkyl isocyanate;

h) Preparation of compound (I)

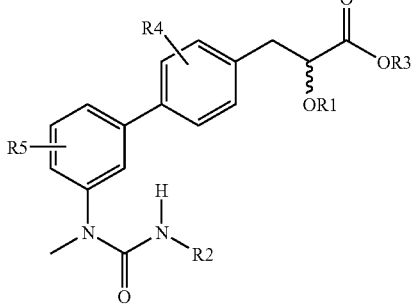

h1) when R3 is an alkyl radical: by transesterification of compound 8 with an alcohol in the presence of an acid, or h2) when R3 is a hydrogen atom: by saponification of compound 8 in the presence of a base.

18. A process for the synthesis of a compound of formula (I) or of an isomer, optical or geometrical, pure or as a mixture, in any proportion, of said compound of formula (I), of the tautomeric form, or of the salt of said compound of formula (I) as defined in claim 1, comprising the following stages:

a) Preparation of the compound of formula 1:

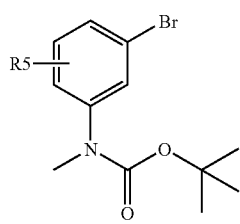

where R5 is a hydrogen atom, a halogen atom, a hydroxyl radical, an alkyl radical having from 1 to 6 carbon atoms, an alkoxy radical, a benzyloxy radical or a trifluoromethyl radical, from 3-bromoaniline, by protecting the amine with di(tert-butyl) dicarbonate and by then carrying out a methylation in the presence of sodium hydride;

b) Preparation of compound 2:

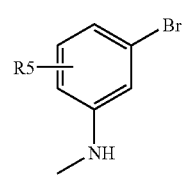

with R5 as defined above, by treating compound 1 with an acid;

c) Preparation of compound 3:

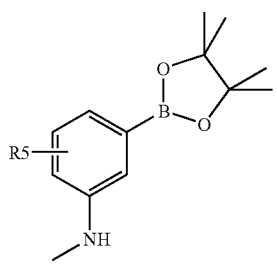

with R5 as defined above, by the reaction of compound 2 with pinacolborane in the presence of a catalyst;

d) Preparation of compound 5:

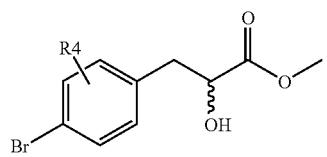

with R4 representing a hydrogen atom, a halogen atom, a hydroxyl radical, an alkyl radical having from 1 to 6 carbon atoms, an alkoxy radical, a benzyloxy radical or a trifluoromethyl radical,
by treating the epoxide 4

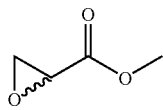

4 with an aryl halide in the presence of tert-butyllithium and of copper cyanide;
   i) Preparation of compound 10:

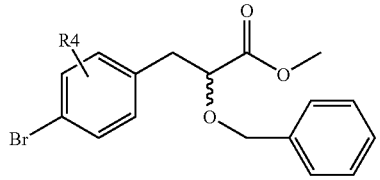

10 with R4 as defined above,
by treating compound 5 with a benzyl halide in the presence of silver oxide;
   j) Preparation of compound 11:

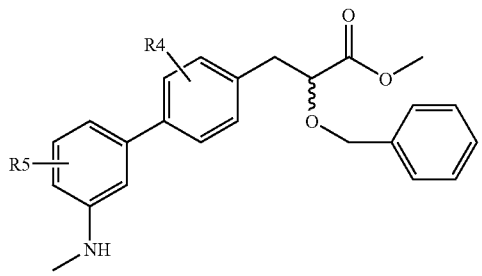

11 with R4 and R5 as defined above,
by coupling compound 10 with compound 3 by a reaction of Suzuki type using a palladium catalyst;
   k) Preparation of compound 12, in which R2, R4 and R5 are as defined in the formula (I),

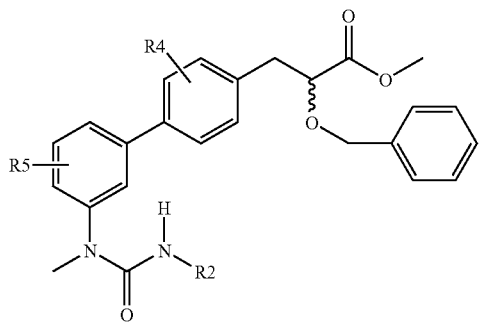

12 with R2 representing an alkyl group having from 3 to 8 carbon atoms and R4 and R5 as defined above,
by the reaction from compound 11 and an alkyl isocyanate;
   l) Preparation of the alcohol 13:

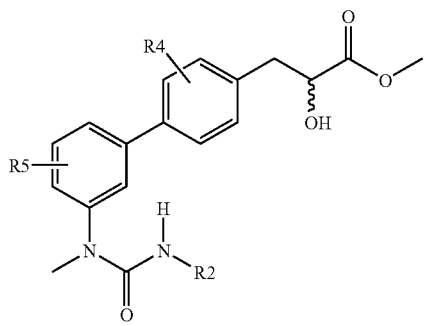

13 with R2, R4 and R5 as defined above,
by hydrogenolysis of compound 12 with hydrogen in the presence of palladium-on-charcoal;
   m) Preparation of compound 8, in which R1, R2, R4 and R5 are as defined in the formula (I),

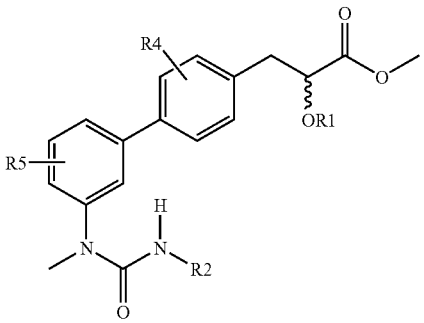

8 with R1 representing an alkyl group having from 1 to 6 carbon atoms, an acetyl group, a methylcyclopropane group, an aralkyl group or an aryl group and R2, R4 and R5 as defined above;
by reacting compound 13 with an alkyl halide in the presence of silver oxide;
   n) Preparation of compound (I):

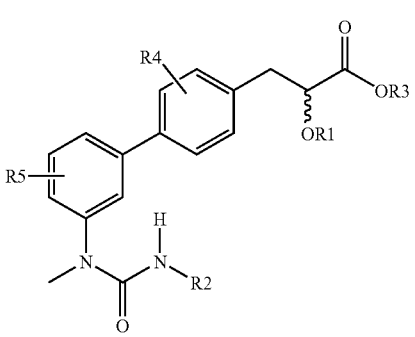

(I)

n1) when R3 is an alkyl radical: by transesterification of compound 8 with an alcohol in the presence of an acid, or n2) when R3 is a hydrogen atom: by saponification of compound 8 in the presence of a base.

19. A biaromatic compound as defined by claim 1, wherein R1 is an alkyl radical selected from the group consisting of methyl, ethyl, n-propyl, cyclopropyl, isobutyl, tert-butyl, n-pentyl, isopentyl, n-hexyl, isohexyl, cyclohexyl, ethylenyl, allyl, propenyl, butenyl, pentenyl and hexenyl.

20. A biaromatic compound as defined by claim 19, wherein R1 is an alkyl radical selected from the group consisting of methyl, ethyl, n-propyl, isopropyl, cyclopropyl, isobutyl and tert-butyl.

21. A biaromatic compound having the following structural formula (I):

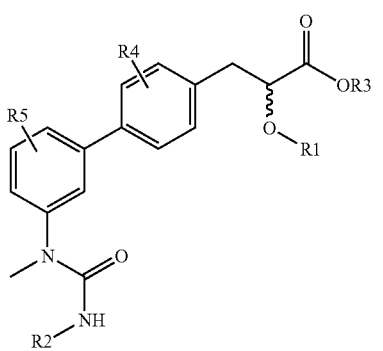

in which:
R1 is a methyl, ethyl, propyl or allyl radical;
R2 is an alkyl radical having 3 to 8 carbon atoms;
R3 is a hydrogen atom or an alkyl radical having 1 to 6 carbon atoms;
R4 and R5, which are identical or different, are each a hydrogen atom, a halogen atom, a hydroxyl radical, an alkyl radical having from 1 to 6 carbon atoms, an alkoxy radical, a benzyloxy radical or a trifluoromethyl radical;

or an isomer, optical or geometrical, pure or as a mixture, in any proportion, of said compound of formula (I) or a tautomeric form, or a salt of said compound of formula (I).

22. The biaromatic compound as defined by claim 19, wherein R2 is an alkyl radical selected from the group consisting of n-pentyl, isopentyl, cyclopentyl, n-hexyl, isohexyl, cyclohexyl, n-heptyl and isoheptyl.

23. The biaromatic compound as defined by claim 20, wherein R2 is an alkyl radical selected from the group consisting of n-pentyl, isopentyl, cyclopentyl, n-hexyl, isohexyl, cyclohexyl, n-heptyl and isoheptyl.

24. The biaromatic compound as defined by claim 21, wherein R2 is an alkyl radical selected from the group consisting of n-pentyl, isopentyl, cyclopentyl, n-hexyl, isohexyl, cyclohexyl, n-heptyl and isoheptyl.

25. The biaromatic compound as defined by claim 19, wherein R3 is a hydrogen atom.

26. The biaromatic compound as defined by claim 20, wherein R3 is a hydrogen atom.

27. The biaromatic compound as defined by claim 21, wherein R3 is a hydrogen atom.

28. The biaromatic compound as defined by claim 19, wherein R4 and R5, which are identical or different, are each a hydrogen atom or a fluorine atom.

29. The biaromatic compound as defined by claim 20, wherein R4 and R5, which are identical or different, are each a hydrogen atom or a fluorine atom.

30. The biaromatic compound as defined by claim 21, wherein R4 and R5, which are identical or different, are each a hydrogen atom or a fluorine atom.

31. The biaromatic compound as defined by claim 22, wherein R3 is a hydrogen atom.

32. The biaromatic compound as defined by claim 23, wherein R3 is a hydrogen atom.

33. The biaromatic compound as defined by claim 24, wherein R3 is a hydrogen atom.

34. The biaromatic compound as defined by claim 22, wherein R4 and R5, which are identical or different, are each a hydrogen atom or a fluorine atom.

35. The biaromatic compound as defined by claim 23, wherein R4 and R5, which are identical or different, are each a hydrogen atom or a fluorine atom.

36. The biaromatic compound as defined by claim 24, wherein R4 and R5, which are identical or different, are each a hydrogen atom or a fluorine atom.

37. The biaromatic compound as defined by claim 25, wherein R4 and R5, which are identical or different, are each a hydrogen atom or a fluorine atom.

38. The biaromatic compound as defined by claim 26, wherein R4 and R5, which are identical or different, are each a hydrogen atom or a fluorine atom.

39. The biaromatic compound as defined by claim 27, wherein R4 and R5, which are identical or different, are each a hydrogen atom or a fluorine atom.

40. The biaromatic compound as defined by claim 21, wherein R1 is ethyl.

41. The biaromatic compound as defined by claim 40, which is 2(S)-ethoxy-3-[3'-(3-heptyl-1-methylureido)biphenyl-4-yl]propanoic acid.

42. The biaromatic compound as defined by claim 21, selected from the group consisting of:
2(S)-Ethoxy-3-[3'-(3-heptyl-1-methylureido)biphenyl-4-yl]propanoic acid,
2(S)-Ethoxy-3-[3'-(1-methyl-3-pentylureido)biphenyl-4-yl]propanoic acid,
2(S)-Propyloxy-3-[3'-(3-heptyl-1-methylureido)biphenyl-4-yl]propanoic acid,
2(S)-Allyloxy-3-[3'-(3-heptyl-1-methylureido)biphenyl-4-yl]propanoic acid,
3-[3'-(1-Methyl-3-pentylureido)biphenyl-4-yl]-2(S)-propoxypropanoic acid,
2(S)-Allyloxy-3-[3'-(1-methyl-3-pentylureido)biphenyl-4-yl]propanoic acid,
2(S)-Methoxy-3-[3'-(1-methyl-3-pentylureido)biphenyl-4-yl]propanoic acid,
3-[3'-(3-Heptyl-1-methylureido)biphenyl-4-yl]-2(S)-methoxypropanoic acid,
2(S)-Ethoxy-3-[3'-(1-methyl-3-propylureido)biphenyl-4-yl]propanoic acid,
3[3'-(3-Cyclopropylmethyl-1-methylureido)biphenyl-4-yl]-2(S)-ethoxypropanoic acid,
3-[3'-(3-Cyclopentylmethyl-1-methylureido)biphenyl-4-yl]-2(S)-ethoxypropanoic acid,
2(S)-Ethoxy-3-[3-fluoro-3'-(1-methyl-3-pentylureido)biphenyl-4-yl]propanoic acid
2(S)-Ethoxy-3-[4'-fluoro-3'-(1-methyl-3-pentylureido)biphenyl-4-yl]propanoic acid
3-[3,4'-Difluoro-3'-(1-methyl-3-pentylureido)biphenyl-4-yl]-2(S)-ethoxypropanoic acid,
Methyl 2(S)-ethoxy-3-[3'-(3-heptyl-1-methylureido)biphenyl-4-yl]propanoate, 3-{3'-[3-(2-Cyclohexylethyl)-1-methylureido]biphenyl-4-yl}-2(S)-ethoxypropanoic acid, 2(R)-Ethoxy-3-[3'-(1-methyl-3-pentylureido)biphenyl-4-yl]propanoic acid, 2(R)-Ethoxy-3-[3'-(3-heptyl-1-methylureido)biphenyl-4-yl]propanoic acid, 2-Ethoxy-3-[3'-(3-heptyl-1-methylureido)biphenyl-4-yl]propanoic acid, 2(R)-Allyloxy-3[3'-(3-heptyl-1-methylureido)biphenyl-4-yl]propanoic acid, 3-[3'-(3-Allyl-1-methylureido)biphenyl-4-yl]-2(S)-ethoxypropanoic acid, and Allyl 3-[3'-(3-allyl-1-methylureido)biphenyl-4-yl]-2(S)-ethoxypropanoate.

43. A biaromatic compound having the following structural formula (I):

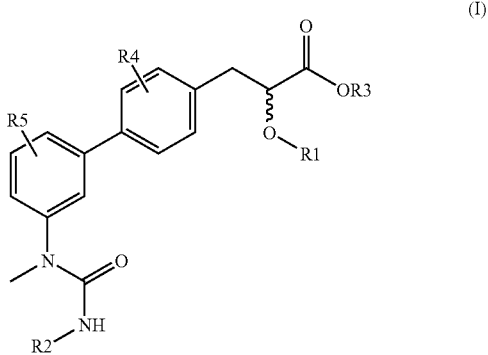

in which:
R1 is methyl, ethyl, allyl, cyclopropylmethyl or benzyl;
R2 is n-pentyl or n-heptyl;
R3 is hydrogen;
R4 and R5, which are identical or different, are a hydrogen atom or a fluorine atom;
and the compound has the (S) configuration at the 2-position of the propionic acid portion of the molecule.

44. The biaromatic compound as defined by claim 43, selected from the group consisting of:

2(S)-Ethoxy-3-[3'-(3-heptyl-1-methylureido)biphenyl-4-yl]propanoic acid,

2(S)-Ethoxy-3-[3'-(1-methyl-3-pentylureido)biphenyl-4-yl]propanoic acid,

2(S)-Cyclopropylmethoxy-3-[3'-(3-heptyl-1-methylureido)biphenyl-4-yl]propanoic acid, 2(S)-Benzyloxy-3-[3'-(3-heptyl-1-methylureido)biphenyl-4-yl]propanoic acid, 2(S)-Allyloxy-3-[3'-(3-heptyl-1-methylureido)biphenyl-4-yl]propanoic acid, 2(S)-Cyclopropylmethoxy-3-[3'-(1-methyl-3-pentylureido)biphenyl-4-yl]propanoic acid, 2(S)-Allyloxy-3-[3'-(1-methyl-3-pentylureido)biphenyl-4-yl]propanoic acid, 2(S)-Benzyloxy-3-[3'-(1-methyl-3-pentylureido)biphenyl-4-yl]propanoic acid, 2(S)-Methoxy-3-[3'-(1-methyl-3-pentylureido)biphenyl-4-yl]propanoic acid, 3-[3'-(3-Heptyl-1-methylureido)biphenyl-4-yl]-2(S)-methoxypropanoic acid, 2(S)-Ethoxy-3-[3-fluoro-3'-(1-methyl-3-pentylureido)biphenyl-4-yl]propanoic acid, 2(S)-Ethoxy-3-[4'-fluoro-3'-(1-methyl-3-pentylureido)biphenyl-4-yl]propanoic acid 3-[3'-Difluoro-3'-(1-methyl-3-pentylureido)biphenyl-4yl]-2(S)-ethoxypropanoic acid, and 3-[3'-(3-Allyl-1-methylureido)biphenyl-4-yl]-2(S)-ethoxypropanoic acid.

45. A cosmetic composition comprising at least one biaromatic compound as defined by claim 21, formulated into a physiologically acceptable medium therefor.

46. The cosmetic composition as defined by claim 45, comprising from 0.001% to 3% by weight of said at least one biaromatic compound.

47. A pharmaceutical composition useful for regulating and/or restoring the metabolism of skin lipids, comprising a thus effective amount of at least one biaromatic compound as defined by claim 21, formulated into a physiologically acceptable medium therefor.

48. A cosmetic composition useful for body and/or hair hygiene, comprising a thus effective amount of at least one biaromatic compound as defined by claim 21, formulated into a cosmetically acceptable medium therefor.

49. The pharmaceutical composition as defined by claim 47, comprising from 0.001% to 10% by weight of said at least one biaromatic compound.

50. The pharmaceutical composition as defined by claim 47, comprising from 0.01 % to 1 % by weight of said at least one biaromatic compound.

51. A cosmetic composition comprising at least one biaromatic compound as defined by claim 43, formulated into a physiologically acceptable medium therefor.

52. The cosmetic composition as defined by claim 51, comprising from 0.001 % to 3% by weight of said at least one biaromatic compound.

53. A pharmaceutical composition useful for regulating and/or restoring the metabolism of skin lipids, comprising a thus effective amount of at least one biaromatic compound as defined by claim 43, formulated into a physiologically acceptable medium therefor.

54. A cosmetic composition useful for body and/or hair hygiene, comprising a thus effective amount of at least one biaromatic compound as defined by claim 43, formulated into a cosmetically acceptable medium therefor.

55. The pharmaceutical composition as defined by claim 53, comprising from 0.001% to 10% by weight of said at least one biaromatic compound.

56. The pharmaceutical composition as defined by claim 53, comprising from 0.01% to 1% by weight of said at least one biaromatic compound.

* * * * *